US008486019B2

(12) United States Patent
White et al.

(10) Patent No.: US 8,486,019 B2
(45) Date of Patent: Jul. 16, 2013

(54) PATIENT MEDICATION IV DELIVERY PUMP WITH WIRELESS COMMUNICATION TO A HOSPITAL INFORMATION MANAGEMENT SYSTEM

(75) Inventors: Gale White, Fort Worth, TX (US);
Roger J. Hill, Richardson, TX (US);
Michael J. Zakrewski, Carrollton, TX (US); Ruth Kummerlen, College Station, TX (US); Martyn Stuart Abbott, Dallas, TX (US); Robert C. Brooks, Mabank, TX (US)

(73) Assignee: B. Braun Medical, Inc., Bethlehem, PA (US)

(*) Notice: Subject to any disclaimer, the term of this patent is extended or adjusted under 35 U.S.C. 154(b) by 476 days.

(21) Appl. No.: 12/428,254

(22) Filed: Apr. 22, 2009

(65) Prior Publication Data
US 2009/0203329 A1 Aug. 13, 2009

Related U.S. Application Data

(60) Division of application No. 10/799,842, filed on Mar. 13, 2004, now Pat. No. 7,645,258, which is a continuation-in-part of application No. 09/702,310, filed on Oct. 31, 2000, now Pat. No. 6,790,198, which is a continuation-in-part of application No. 09/452,488, filed on Dec. 1, 1999, now Pat. No. 6,519,569.

(51) Int. Cl.
*A61M 1/00* (2006.01)

(52) U.S. Cl.
USPC .......................................................... 604/151

(58) Field of Classification Search
USPC ............... 604/65–67, 151, 131; 128/DIG. 12, 128/DIG. 13
See application file for complete search history.

(56) References Cited

U.S. PATENT DOCUMENTS 3,715,570 A 2/1973 Weichselbaum et al.
3,780,907 A 12/1973 Colburn et al.
(Continued)

FOREIGN PATENT DOCUMENTS

CA 1293566 12/1991
CA 2055952 4/1993
(Continued)

OTHER PUBLICATIONS

Request for Ex Parte Reexamination, Jun. 22, 2009 (133 pages, not attached; available via Public).
(Continued)

*Primary Examiner* — Manuel Mendez
(74) *Attorney, Agent, or Firm* — Osha Liang LLP; John W. Montgomery

(57) ABSTRACT

A wireless communication system from an IV medication infusion pump to a hospital information management system (HIMS) is disclosed. The system includes an IV pump having pump operation circuitry for monitoring pre-selected characteristics of pump operation indicative of IV administration of medication to a patient. A transmitter or transceiver is connected to the pump operation circuitry for receiving a wireless pump signal representing instructional data to the IV pump and for transmitting a wireless pump signal representing the pre-selected pump operation characteristics. The wireless pump transmitter or transceiver communicates with a hospital information management system (HIMS). The HIMS includes a receiver or transceiver capable of transmitting and receiving the pump signal representing the pump operation characteristics and also includes a computer processor capable of storing and displaying the pump operation characteristics that are represented by the received wireless pump signal. In one embodiment, is a medication order transmitter capable of receiving doctor order input and transmitting a signal representing a pumping operation to the HIMS for comparison to pump operation characteristics represented by the pump signal.

5 Claims, 8 Drawing Sheets

U.S. PATENT DOCUMENTS

| | | |
|---|---|---|
| 3,826,900 A | 7/1974 | Moellering |
| 3,831,006 A | 8/1974 | Chaffin, III et al. |
| 3,848,112 A | 11/1974 | Weichselbaum et al. |
| 3,898,984 A | 8/1975 | Mandel |
| 3,917,045 A | 11/1975 | Williams et al. |
| 3,921,196 A | 11/1975 | Patterson |
| 4,121,574 A | 10/1978 | Lester |
| 4,308,866 A | 1/1982 | Jelliffe et al. |
| 4,473,884 A | 9/1984 | Behl |
| 4,491,725 A | 1/1985 | Pritchard |
| 4,523,087 A | 6/1985 | Benton |
| 4,560,979 A | 12/1985 | Rosskopf |
| 4,628,193 A | 12/1986 | Blum |
| 4,636,950 A | 1/1987 | Caswell et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,741,732 A | 5/1988 | Crankshaw et al. |
| 4,767,917 A | 8/1988 | Ushikubo |
| 4,810,243 A | 3/1989 | Howson |
| 4,828,545 A | 5/1989 | Epstein et al. |
| 4,839,806 A | 6/1989 | Goldfischer et al. |
| 4,893,270 A | 1/1990 | Beck et al. |
| 4,943,279 A | 7/1990 | Samiotes et al. |
| 4,953,745 A | 9/1990 | Rowlett, Jr. |
| 5,036,852 A | 8/1991 | Leishman |
| 5,041,086 A | 8/1991 | Koenig et al. |
| 5,072,383 A | 12/1991 | Brimm et al. |
| 5,078,683 A | 1/1992 | Sancoff et al. |
| 5,088,981 A | 2/1992 | Howson et al. |
| 5,100,380 A | 3/1992 | Epstein et al. |
| 5,113,869 A | 5/1992 | Nappholz et al. |
| 5,179,569 A | 1/1993 | Sawyer |
| 5,208,762 A | 5/1993 | Charhut et al. |
| 5,253,361 A | 10/1993 | Thurman et al. |
| 5,276,611 A | 1/1994 | Ghiraldi |
| 5,291,399 A | 3/1994 | Chaco |
| 5,292,029 A | 3/1994 | Pearson |
| 5,302,093 A | 4/1994 | Owens et al. |
| 5,314,243 A | 5/1994 | McDonald et al. |
| 5,317,506 A | 5/1994 | Coutre et al. |
| 5,319,543 A | 6/1994 | Wilhelm |
| 5,338,157 A | 8/1994 | Blomquist |
| 5,342,298 A | 8/1994 | Michaels et al. |
| 5,367,555 A | 11/1994 | Isoyama |
| 5,376,070 A | 12/1994 | Purvis et al. |
| 5,390,236 A | 2/1995 | Klausner et al. |
| 5,395,320 A | 3/1995 | Padda et al. |
| 5,445,621 A | 8/1995 | Poli et al. |
| 5,451,760 A | 9/1995 | Renvall |
| 5,455,851 A | 10/1995 | Chaco et al. |
| 5,456,691 A | 10/1995 | Snell |
| 5,458,123 A | 10/1995 | Unger |
| 5,465,082 A | 11/1995 | Chaco |
| 5,485,408 A | 1/1996 | Blomquist |
| 5,490,610 A | 2/1996 | Pearson |
| 5,505,696 A | 4/1996 | Miki |
| 5,529,063 A | 6/1996 | Hill |
| 5,531,679 A | 7/1996 | Schulman et al. |
| 5,539,836 A | 7/1996 | Babkin |
| 5,542,420 A | 8/1996 | Goldman et al. |
| 5,547,470 A | 8/1996 | Johnson et al. |
| 5,554,013 A | 9/1996 | Owens et al. |
| 5,560,529 A | 10/1996 | Udagawa et al. |
| 5,562,621 A | 10/1996 | Claude et al. |
| 5,573,506 A | 11/1996 | Vasko |
| 5,582,593 A | 12/1996 | Hultman |
| 5,591,344 A | 1/1997 | Kenley et al. |
| 5,594,786 A | 1/1997 | Chaco et al. |
| 5,597,995 A | 1/1997 | Williams et al. |
| 5,630,710 A | 5/1997 | Tune et al. |
| 5,640,301 A | 6/1997 | Roecker et al. |
| 5,658,250 A | 8/1997 | Blomquist et al. |
| 5,683,367 A | 11/1997 | Jordan et al. |
| 5,697,899 A | 12/1997 | Hillman et al. |
| 5,700,998 A | 12/1997 | Palti |
| RE35,743 E | 3/1998 | Pearson |
| 5,732,401 A | 3/1998 | Conway |
| 5,764,159 A * | 6/1998 | Neftel ................ 340/870.09 |
| 5,781,442 A * | 7/1998 | Engleson et al. ............. 700/214 |
| 5,782,805 A | 7/1998 | Meinzer et al. |
| 5,788,669 A | 8/1998 | Peterson |
| 5,793,861 A | 8/1998 | Haigh |
| 5,795,327 A | 8/1998 | Wilson et al. |
| 5,797,515 A | 8/1998 | Liff et al. |
| 5,803,917 A | 9/1998 | Butterfield et al. |
| 5,807,336 A | 9/1998 | Russo et al. |
| 5,813,972 A | 9/1998 | Nazarian et al. |
| 5,814,015 A | 9/1998 | Gargano et al. |
| 5,822,418 A | 10/1998 | Yacenda et al. |
| 5,822,544 A | 10/1998 | Chaco et al. |
| 5,827,223 A | 10/1998 | Butterfield |
| 5,842,976 A | 12/1998 | Williamson |
| 5,848,593 A | 12/1998 | McGrady et al. |
| 5,848,988 A | 12/1998 | Davis |
| 5,852,590 A | 12/1998 | De La Huerga |
| 5,855,550 A | 1/1999 | Lai et al. |
| 5,865,745 A | 2/1999 | Schmitt et al. |
| 5,883,576 A | 3/1999 | De La Huerga |
| 5,885,245 A | 3/1999 | Lynch et al. |
| 5,888,052 A | 3/1999 | Hill |
| 5,895,371 A | 4/1999 | Levitas et al. |
| 5,903,889 A | 5/1999 | de la Huerga et al. |
| 5,912,818 A | 6/1999 | McGrady et al. |
| 5,913,197 A | 6/1999 | Kameda |
| 5,923,018 A | 7/1999 | Kameda et al. |
| 5,924,074 A | 7/1999 | Evans |
| 5,935,099 A | 8/1999 | Peterson et al. |
| 5,939,699 A | 8/1999 | Perttunen et al. |
| 5,941,846 A | 8/1999 | Duffy et al. |
| 5,943,633 A | 8/1999 | Wilson et al. |
| 5,945,651 A | 8/1999 | Chorosinski et al. |
| 5,960,085 A | 9/1999 | De La Huerga |
| 5,961,487 A | 10/1999 | Davis |
| 5,971,593 A | 10/1999 | McGrady |
| 5,993,046 A | 11/1999 | McGrady et al. |
| 6,003,006 A | 12/1999 | Colella et al. |
| 6,009,333 A | 12/1999 | Chaco |
| 6,018,713 A | 1/2000 | Coli et al. |
| 6,021,392 A | 2/2000 | Lester et al. |
| 6,024,539 A | 2/2000 | Blomquist |
| 6,032,155 A | 2/2000 | De La Huerga |
| 6,039,251 A | 3/2000 | Holowko et al. |
| 6,053,887 A | 4/2000 | Levitas et al. |
| 6,055,458 A | 4/2000 | Cochran et al. |
| 6,068,156 A | 5/2000 | Liff et al. |
| 6,082,776 A | 7/2000 | Feinberg |
| 6,083,248 A | 7/2000 | Thompson |
| 6,109,774 A | 8/2000 | Holmes et al. |
| 6,110,152 A | 8/2000 | Kovelman |
| 6,116,461 A | 9/2000 | Broadfield et al. |
| 6,135,949 A | 10/2000 | Russo et al. |
| 6,139,495 A | 10/2000 | De La Huerga |
| 6,150,942 A | 11/2000 | O'Brien |
| 6,152,364 A | 11/2000 | Schoonen et al. |
| 6,158,965 A | 12/2000 | Butterfield et al. |
| 6,170,746 B1 | 1/2001 | Brook et al. |
| 6,189,727 B1 | 2/2001 | Shoenfeld |
| 6,190,441 B1 | 2/2001 | Czabala et al. |
| 6,210,361 B1 | 4/2001 | Kamen et al. |
| 6,213,972 B1 | 4/2001 | Butterfield et al. |
| 6,234,997 B1 | 5/2001 | Kamen et al. |
| 6,241,704 B1 | 6/2001 | Peterson et al. |
| 6,283,322 B1 | 9/2001 | Liff et al. |
| 6,292,698 B1 | 9/2001 | Duffin et al. |
| 6,317,719 B1 | 11/2001 | Schrier et al. |
| 6,321,203 B1 | 11/2001 | Kameda |
| RE37,531 E | 1/2002 | Chaco et al. |
| 6,347,329 B1 | 2/2002 | Evans |
| 6,352,200 B1 | 3/2002 | Schoonen et al. |
| 6,363,282 B1 | 3/2002 | Nichols et al. |
| 6,364,834 B1 | 4/2002 | Reuss et al. |
| 6,370,841 B1 | 4/2002 | Chudy et al. |
| 6,434,569 B1 | 8/2002 | Toshimitsu et al. |
| 6,449,927 B2 | 9/2002 | Hebron et al. |
| 6,464,667 B1 | 10/2002 | Kamen et al. |

| | | | |
|---|---|---|---|
| 6,475,146 B1 | 11/2002 | Frelburger et al. | |
| 6,507,868 B2 | 1/2003 | Simmon et al. | |
| 6,519,569 B1 | 2/2003 | White et al. | |
| 6,544,228 B1 | 4/2003 | Heitmeier | |
| 6,736,759 B1 | 5/2004 | Stubbs et al. | |
| 6,779,024 B2 | 8/2004 | DeLaHuerga | |
| 6,790,198 B1 | 9/2004 | White et al. | |
| 6,796,956 B2 | 9/2004 | Hartlaub et al. | |
| 6,958,706 B2 | 10/2005 | Chaco et al. | |
| 6,969,369 B2 | 11/2005 | Struble | |
| 2001/0044731 A1 | 11/2001 | Coffman et al. | |
| 2002/0016719 A1 | 2/2002 | Nemeth et al. | |
| 2002/0026330 A1 | 2/2002 | Klein | |
| 2002/0038392 A1 | 3/2002 | De La Huerga | |
| 2002/0046346 A1 | 4/2002 | Evans | |
| 2002/0077865 A1 | 6/2002 | Sullivan | |
| 2002/0082480 A1 | 6/2002 | Riff et al. | |
| 2002/0107707 A1 | 8/2002 | Naparstek et al. | |
| 2002/0169636 A1 | 11/2002 | Eggers et al. | |
| 2002/0174105 A1 | 11/2002 | De La Huerga | |

FOREIGN PATENT DOCUMENTS

| | | | |
|---|---|---|---|
| CA | 2131077 | | 5/1995 |
| CA | 2110774 | | 6/1995 |
| CA | 2145714 | | 10/1995 |
| CA | 2178518 | | 12/1996 |
| DE | 9308204.5 | | 9/2003 |
| EP | 0112699 | | 7/1984 |
| GB | 2279784 | | 1/1995 |
| WO | 88/04073 | A1 | 6/1988 |
| WO | 93/12828 | A1 | 7/1993 |
| WO | 93/21978 | | 11/1993 |
| WO | 94/05355 | A1 | 3/1994 |
| WO | 94/07553 | A1 | 4/1994 |
| WO | 96/27163 | | 9/1996 |
| WO | 96/36923 | | 11/1996 |
| WO | 99/10029 | | 3/1999 |
| WO | 00/03344 | | 1/2000 |
| WO | 00/60522 | | 10/2000 |
| WO | 01/01321 | | 1/2001 |
| WO | 01/08077 | | 2/2001 |
| WO | 01/39816 | | 6/2001 |
| WO | 01/88828 | | 11/2001 |
| WO | 02/36044 | A2 | 5/2002 |

OTHER PUBLICATIONS

Notice of Ex Parte Reexamination filed Jun. 22, 2009 in related patent of US Pat. 6,790,198 (1 page).
Notice of Assignment of Reexamination Request dated Jul. 15, 2009 re US Pat. 6,790,198 (1 page).
Ex Parte Reexamination Communication granting reexamination in related US Pat. 6,790,198 (16 pages), date: Aug. 27, 2009.
Office Action in Ex Parte Reexamination of US Pat. 6,790,198 mailed Jan. 15, 2010(22 pages).
Response to Office Action in Ex Parte Reexamination of US Pat. 6,790,198 dated Mar. 15, 2010 (54 pages).
Reexamination Supplemental Amendment filed Mar. 26, 2010 for US Pat. 6,790,198 (23 pages).
Examiner's Interview Summary of Apr. 27, 2010 based on Engleson mailed May 5, 2010 for US Pat. 6,790,198 (4 pages).
Patent Owner's Statement of Apr. 27, 2010 Interview related to US Pat. 6,790,198 filed May 19, 2010 (6 pages).
Examiner's Summary of May 17, 2010 and May 25, 2010 Interviews mailed May 25, 2010 for US Pat. 6,790,198 (3 pages).
Patent Owner's Statement of May 17, 2010 and May 25, 2010 Interviews filed Jun. 11, 2010 for US Pat. 6,790,198 (6 pages).
Ex Parte Reexamination Certificate, No. 6,790,198 C1 dated Aug. 31, 2010, White et al. from related patent.
Supplementary European Search Report in related European Patent Application No. 05725512.7 mailed Nov. 25, 2010 (47 pages).
PDMS—Patient Data Management System—System Description; Hewlett Packard (Jan. 1982).
PDMS—Patient Data Management System—Clinical User's Guide; Hewlett Packard (Jan. 1982).
ULTICARE—a bedside patient care information system; Health Data Sciences (Oct. 1984).
John E. Brimm, MD, "Computers in Critical Care"; Critical Care Nursing Quarterly 1987; 9(4); 53-63.
P.C. Tang, et al. "Semantic integration of information in a physician's workstation", Feb. 1994, pp. 47-60, International Journal of Bio-Medical Computing, vol. 35, No. 1, XP000434738.
L. Kleinholz, et al., "Supporting Cooperative Medicine: The Bermed Project", Dec. 1994, pp. 44-53, IEEE Multimedia, vol. 1, No. 4, XP000484150.
PDMS—Patient Data Management System—System Description; Hewlett Packard (Jan. 1992).
Monthly New Medicine, Jul. 1993; No. 223; pp. 62-64.
Monthly New Medicine; Jul. 1993; No. 223; pp. 44-49.
Yasushi Horichi et al., "Image Diagnosis and Radioactive Ray Medical Care Series 6th II Examples", Recent Manner to Think and Existence of Radioactive Ray, No. 6, vol. 37, No. 5, Sep. 1995, pp. 483-490.
Katsuhiro Ohashi et al., "Outpatient Clinic by Use of Electronic Chart", Japan Journal of Medical Informatics, vol. 10, No. 3, Dec. 1990, pp. 227-242.
13th Medical Informatics United Meeting Thesis; pp. 665-666; Nov. 25-27, 1993.
Communication pursuant to Article 94(3) EPC issued in related EP case Serial No. 05725512.7-2320 dated Mar. 23, 2011 (3 pages).
Notice of Opposition in related matter EP1355597 dated Sep. 1, 2010 with English translation; (46 pages).
Communication of Notice of Opposition in related matter EP1355597 dated Sep. 13, 2010 (1 page).
ETSI TS 100 905 V7.0.0, published Aug. 1999 (21 pages).
Blutreinigungsverfahren, editor: H.E. Franz, Georg Thieme Verlag Stuttgart, New York; chapter 5, pp. 50-62, Technik der Hämodialyse' (D. Bundschu, H. Kraker), published 1981 (no English translation)(16 pages).
Communication of Notices of Opposition dated Oct. 7, 2010 in related matter EP1355597 (1 page).
Response to the Communication of Notices of Opposition (Rule 79(1) EPC) dated Oct. 7, 2010 (37 pages).
Summons to attend oral proceedings pursuant to Rule 115(1) EPC in related matter EP1355597 dated Jul. 29, 2011, (10 pages).
Opponent's Response to the Summons to Attend Oral Proceedings dated Jul. 29, 2011 and the written submissions of the patent proprietor of Feb. 7, 2011 in related matter EP1355597, (8 pages).
Communication of Notice of Opposition (R. 79(1) EPC) in related matter EP1237590 dated Aug. 10, 2011 (20 pages).
Applicant's Response to the Communication of Notices of Opposition (Rule 79(1) EPC) dated Aug. 10, 2011 in related matter EP1237590 (29 pages).
Reexamination Office Action SN 95002104 mailed Nov. 1, 2012 (71 pages).

* cited by examiner

PATIENT MEDICATION IV DELIVERY PUMP WITH WIRELESS COMMUNICATION TO A HOSPITAL INFORMATION MANAGEMENT SYSTEM

CROSS-REFERENCE TO RELATED APPLICATIONS

This is a divisional of application titled "Patient Medication IV Delivery Pump with Wireless Communication to a Hospital Information Management System", Ser. No. 10/799,842, filed Mar. 13, 2004, issued as U.S. Pat. No. 7,645,258, which is a continuation-in-part of application titled "Patient Medication IV Delivery Pump With Wireless Communication To A Hospital Information Management System," Ser. No. 09/702,310, filed Oct. 31, 2000, issued as U.S. Pat. No. 6,790,198, and for which a reexamination certificate issued under 37 U.S.C. 307, which is a continuation-in-part of application titled "Improved Security Infusion Pump With Bar Code Reader," Ser. No. 09/452,488, filed Dec. 1, 1999, issued as U.S. Pat. No. 6,519,569, and incorporated herein by reference and relied upon for priority.

TECHNICAL FIELD OF THE INVENTION

The present invention relates to an intravenous (IV) infusion pump for use in a health care facility, such as a hospital. The pump is designed to provide enhanced monitoring and record keeping of infusion pump operations and operational characteristics, such as settings, parameters, conditions or states, through a hospital information management system (HIMS).

BACKGROUND OF THE INVENTION

In hospitals there is a need to accurately monitor the administration of medications to patients. Presently systems for administration of IV medications to a patient in a hospital vary from hospital to hospital in certain specific aspects. However, many basic procedures and practices are similar in a significant number of hospitals for the administration of medications. For example, the administration of medication to a patient, originate with prescribed medications ordered by a doctor. The doctor's order is provided to a pharmacy where a trained pharmacist obtains and prepares the ordered medication. In the case of medications to be administered orally (as with pills), intramuscularly (as with a needle and syringe) or intravenously (as with a mixture of medication in a diluent), the pharmacist may provide the medication for delivery to the patient's nurse with appropriate instructions for administering the medication to the patient according to the doctor's order.

In the case of pills or injections, the pharmacist delivers the pills or a vile for the injection with instructions for the quantity or the amount to be administered.

In the case of an IV medication, the pharmacist prepares an IV solution according to the doctor's order. Typically the resulting IV solution is prepared in a sterile bag in the form of a diluent and the active medication. Often the diluent includes sodium chloride or glucose in water for hydrating and nourishing the patient. Other medications may also be included as may facilitate medical treatment.

In the case of a blood product that requires IV administration, the doctor's order is usually provided to a hospital lab. Where the hospital laboratory prepares a blood product for administration to a patient, the blood product will typically be provided in a sterile IV hanging bag.

A prepared IV medication solution or blood product is labeled; identifying the patient, identifying the medication (or the blood product) and indicating the appropriate administration instructions according to the Doctor's order. The non-IV medication, the IV medication or the blood product is then delivered to the hospital floor where the patient is residing. Typically all medication goes to a nurse's station on the designated floor and the nurse who is assigned to the patient administers and documents the administration of the medication.

In the past, monitoring each step of the process from the doctor's order to the pharmacist, to preparation of the medication, to the laboratory preparation of the blood product and to the administration to the patient was by handwritten or typed documentation. The doctor, the pharmacy, the lab and the nurse who actually administers the medication to the patient make separate entries.

The record of medication administration to the patient by the nurse might be a single entry on the patient's chart at the time the medication is given. In the case of oral or intramuscular medications, this record might be sufficient. In the case of an IV medication the administering event actually occurs over an extended period of time during which numerous situations could interfere with complete administration of the medication to the patient and the single event entry may be inadequate.

Modern hospitals have developed central systems using sophisticated computer equipment to help keep track of patients and to monitor the health care services provided to them. These systems including central computer monitoring are sometimes known as Hospital Information Management Systems (HIMS). Typically a patient is given a unique patient identification number when admitted to the hospital. This number is placed on the patient's chart and often on a patient ID bracelet. Selected information known at the time of patient admission to the hospital, for example, information relevant to the patient, the patient's physician, the method of payment or insurance coverage, the patient's condition, initial diagnosis, intended treatment and etc. can be entered into the HIMS at the admissions desk. Other information that might become known or that subsequently becomes relevant during the hospital stay might also be entered into a properly programmed HIMS. The HIMS presents possibilities for allowing useful information retrieval by authorized healthcare providers in the hospital, whether it be the attending physician, the ER doctors, "on call" physicians, nurses, pharmacist, lab technicians and etc. Privacy can be maintained for portions of the information that is relevant to financial operations or other sensitive information under appropriate access codes or using other procedures. For example, information such as cost of medications, supplies and special services associated with the patient's care, can be stored and coded for the particular patient and accessed by billing clerks, insurance administrators, and account coordinators, to maintain patient privacy.

Much of the patient information is currently typed into the computer through network computer terminals wired to the HIMS. It is difficult to keep certain types of information current, particularly specific patient care information from the patient's hospital room chart. The lag time between providing the care or medication to the patient, writing it on the chart and then entering the charted information into the HIMS at a designated network computer or a data entry terminal often entails a significant delay. Also, appropriately tracking the hospital's inventory and patient use of medications and controlled substances such as addictive drugs is not as current or as accurate as might be hoped.

Modern healthcare, particularly in hospitals, clinics and other healthcare institutions, has improved significantly with the development and use of medical infusion pumps to enhance patient care. For example, using a medical infusion pump for parenteral infusion and, in particular, for intravenous infusion directly into the patient's circulatory system, can be facilitate good patient care. Therapeutic fluids, drugs, medications, pharmacological fluids, hydrating fluids, sucrose fluids, nutrient fluids, or other therapeutic fluids can generally be infused using disposable cassette pumps and peristaltic pumps. Syringe pumps can also be used in some instances. Particularly, it is useful to provide different kinds of controlled infusion including rate controlled infusion, periodic infusion, and bolus dosage infusion, all depending upon the medication, the patient, the patient's condition and any of a number of other healthcare considerations.

In institutional healthcare facilities, such as major hospitals, large clinics and other large medical facilities, prescribed medications are prepared in a facility pharmacy by a staff pharmacist or a team of pharmacists, according to a doctor's order. Detailed instructions, for the administration of the drug according to the doctor's order and according to professional knowledge of the pharmacist with respect to pharmacological protocol for the medication, therapeutic fluids or mixtures of drugs involved, may also be provided along with the prescribed medication placed in the hands of nurses or other highly trained medical professionals. The medication is provided for delivery to the patient's room by a nurse or a medical professional, in an appropriate container prepared by the pharmacist along with any appropriate instructions. The medication is then administered to the patient according to the instructions. For purposes of accurate infusion, rather than merely using a timed drip-type infusion mechanism, infusion pumps are useful. The protocol for administering a modern infusion therapeutic fluid may include carefully controlled infusion rates that are based upon the type of medication prescribed. Modern infusion pumps may be adjustably configured to deliver the fluid according to instructions provided by the doctor and/or the pharmacist, by the person administering the infusion.

SUMMARY OF THE INVENTION

A wireless communication system from an IV medication infusion pump to a hospital information management system (HIMS) is disclosed. The system includes an IV pump having pump operation circuitry for monitoring pre-selected characteristics of pump operation indicative of IV administration of medication to a patient. A transmitter or transceiver is connected to the pump operation circuitry for receiving a wireless pump signal representing instructional data to the IV pump and for transmitting a wireless pump signal representing the pre-selected pump operation characteristics. The wireless pump transmitter or transceiver communicates with a hospital information management system (HIMS). The HIMS includes a transceiver capable of transmitting and receiving the pump signal representing the pump operation characteristics and also includes a computer processor capable of storing and displaying the pump operation characteristics that are represented by the received wireless pump signal. In one embodiment, is a medication order transmitter capable of receiving doctor order input and transmitting a signal representing a pumping operation to the HIMS for comparison to pump operation characteristics represented by the pump signal.

BRIEF DESCRIPTION OF THE DRAWINGS

The foregoing objects, advantages, and features, as well as other objects and advantages, will become more apparent with reference to the description and drawings below, in which like numerals represent like elements and in which.

DETAILED DESCRIPTION

Figure 1:
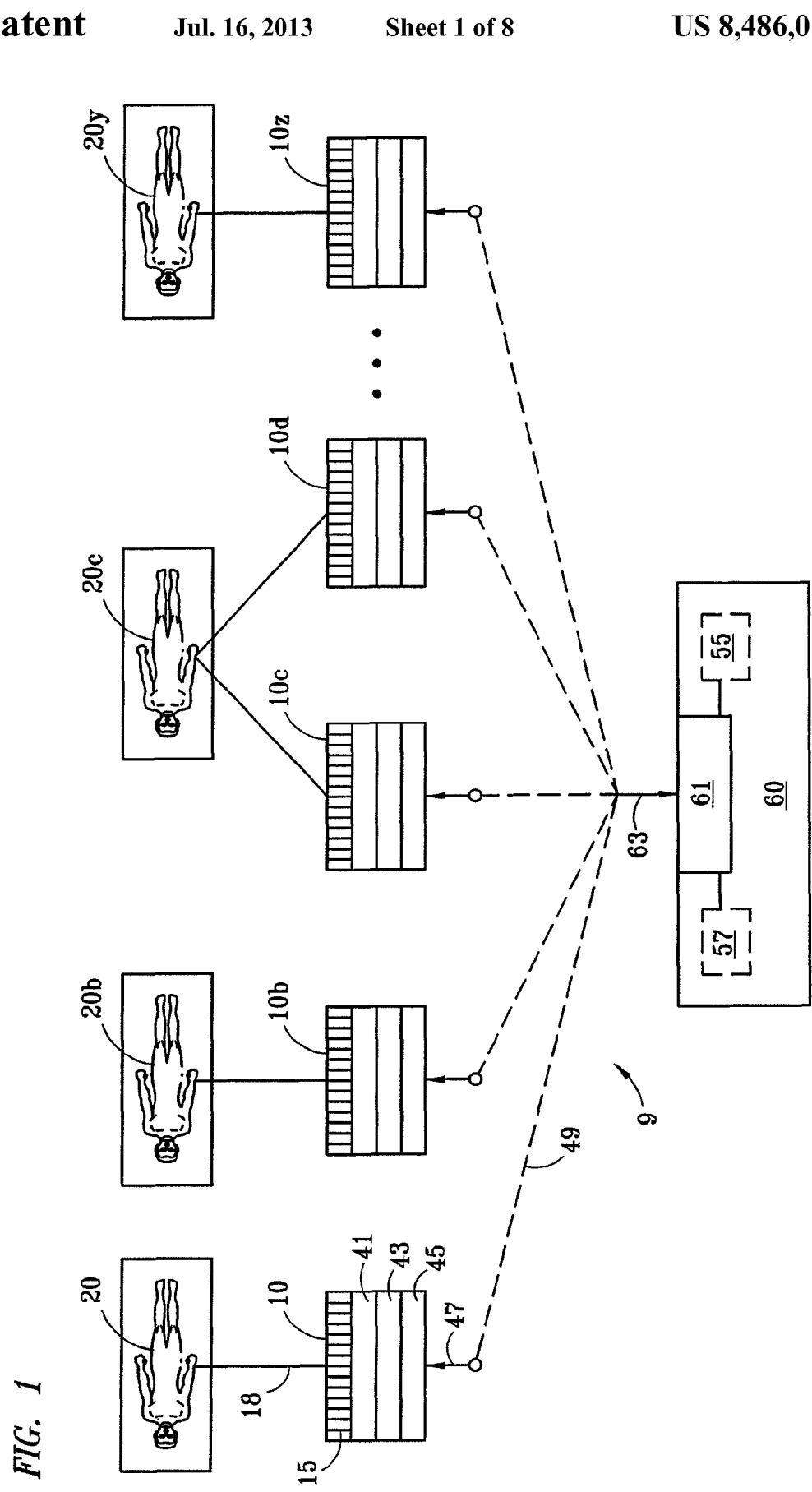
FIG. 1 is a schematic depiction of a hospital system with a plurality of IV pumps with wireless transmission to or from an HIMS.

An embodiment of a wireless communication system 9 is shown schematically in FIG. 1, permitting wireless signal communication from an IV medication infusion pump 10 to a health care facility information center such as a hospital information management system (HIMS) 60. The wireless communication system 9 includes at least one IV pump 10 having pump operation circuitry 41 and circuitry 43 for monitoring pre-selected characteristics 15 of pump operation indicative of IV administration 18 of medication to a patient 20. A transmitter 45 is connected to the IV pump operation circuitry 41 for transmitting a wireless pump signal 49 representing the pre-selected pump operation characteristics 15. Such pump operation characteristics might include any one or more of pump settings, parameters, conditions, states or changes thereof. The wireless pump transmitter 45 wirelessly transmits the pump operation characteristics 15 to the HIMS 60. The HIMS includes a receiver 61 capable of receiving the pump signal 49 representing the pump operation characteristics 15. The HIMS may also include a computer processor 57 capable of storing and displaying at 63 the pump operation characteristics 15 represented by the received wireless pump signal 49.

FIG. 1 also depicts an embodiment comprising a plurality of IV pumps 10, 10b, 10c, 10d, and . . . 10z providing IV medication infusion to a plurality of patients 20, 20b, 20c, 20d, and . . . 20y. It will be understood from the disclosure that any number of pumps 10 may be included in the hospital system for IV infusion to any number of patients 20. Also more than one pump may be provided for any one of the patients. Each of the wireless infusion pumps shall be identified with a unique pump ID such as an identification code, a wireless signal identifier or a digital "address." Similarly, each patient is individually identified with a patient ID for proper security and tracking in the HIMS. Thus each of the plurality of IV pumps can wirelessly communicate with the HIMS and the information regarding the particular pump can be identified and information from the pump regarding the particular patient to whom the identified pump is infusing can be properly identified and tracked in the HIMS. The separate signals are schematically represented as wireless signals 49, 49b, 49c, 49d, and . . . 49z from each pump to the receiver 61 of the HIMS 60. In the embodiment depicted, the wireless signal is depicted as being transmitted for a radio frequency (RF) signal from an antenna 47b at the pump 10 to an RF antenna 63 at the HIMS. It will be understood from the disclosure that while an RF wireless signal is contemplated as a useful for the invention, other wireless signals such as infrared (IR), laser beam, and ultrasonic signals might be used according to some of the aspects of the invention.

Figure 2:
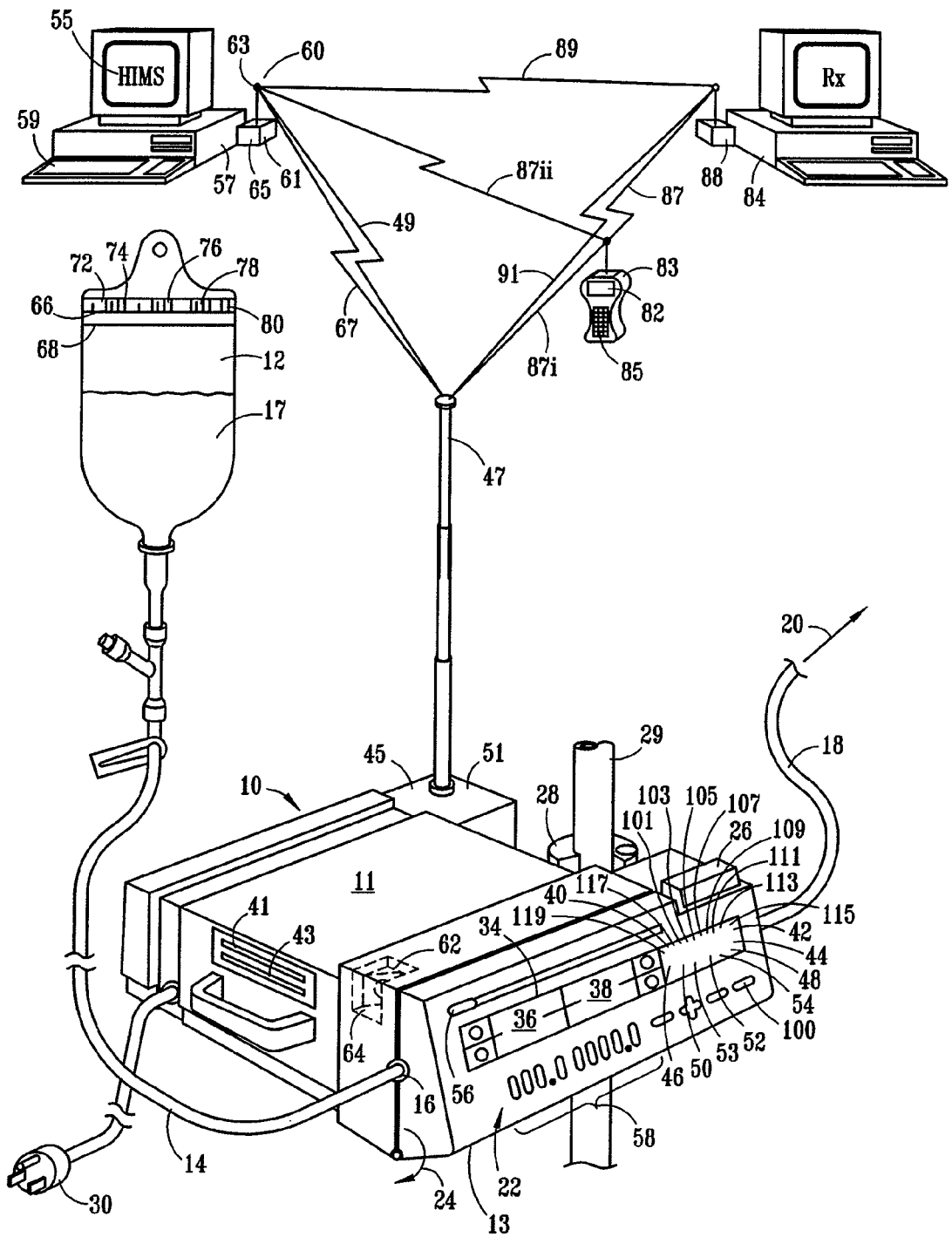
FIG. 2 is a schematic perspective view of an infusion pumping device having a wireless signal transmitter or transceiver according to one embodiment of the present invention.

FIG. 2 shows a schematic perspective view of an infusion pump 10 according to one aspect of the present invention. In this embodiment the pumping device 10 and its various components are generally enclosed within a housing 11. The pumping device 10 pumps a medicinal fluid 17 from a container 12 to provide the fluid 17 to the patient. The container 12, may be a medical bottle or disposable fluid bag or other container capable of holding the required medicinal fluid 17 and the container 12 appropriately interfaces with the pumping device 10 as with medical tubing or delivery other conduits or channels. Fluid 17 is provided from the container 12 through input tube 14. For example, the input tube 14 may be plastic tubing such as medical grade material or silicon tubing. Although a cassette pump is depicted in FIG. 1, it will be understood that the disclosed principles of wireless transmission of pumping information from an IV pump to an HIMS, may similarly be applicable to a peristaltic pump or other appropriate infusion pumps or alternative modes of IV pumping. The input tube 14 carries the fluid into the pumping device 10 through access opening 16. Those skilled in the art will understand form the present disclosure that the access opening 16 may lead to a disposable pumping cassette (not shown) held by door 13, as set forth and described in U.S. Pat. Nos. 5,302,093 and 5,554,013 incorporated by reference herein, or alternatively, may be engaged by door 13 in a peristaltic pumping mechanism (not shown) such as the linear peristaltic pumping mechanism as disclosed in U.S. Pat. Nos. 5,660,529 and 5,888,052, which are also incorporated herein by reference, or may otherwise conduct fluid to the pump depending upon the type of pump. The fluid 17 is actively moved through the pump 10, and is carried through an IV tubing 18 to a patient 20. The flow is schematically represented by arrow 20 in FIG. 2. Control of the pumping rate, pumping volume, pumping time and safety limits is generally addressed through a control panel 22. In the embodiment depicted in FIG. 2, the control panel 22 is connected at a hinge 24 and swings open as indicated by an arrow at hinge 24. This allows the pump 10 to accept an administration set attached by tube 14 to IV container 12. In the case of a peristaltic pump, the pump opens to accept and engage the tubing 14 directly into the peristaltic pumping mechanism. (Other types of pumps might have other arrangements with or without a full or partial door, a hinged or a hinged control panel). The pump door 13 is released using a release lever 26. The entire IV pumping mechanism is shown attached through a pole clamp 28 to a pump-mounting pole 29. Other modes of supporting the pump can be used. The pump is provided with power 30, schematically represented as an electrical plug 30, in one embodiment. Other types or sources of power, such as battery power may be used. For example, a battery back-up system might be appropriately included within the pump for maintaining operations and/or for maintaining stored data or transmitting an alarm condition signal, transmitting pump operational information, operational log data or other data stored at the IV pump 10.

The IV pump 10 is provided with a visual display panel 34 that is conveniently and usefully formed on the control panel 22. This control panel 22 is provided with a visual display panel 34 to visually show selectably entered adjustable pump operational characteristics and characteristics. For example, but without limiting the nature of the display panel 34 to a particular configuration, separate displays or sectioned display areas might include infusion rate display 36, volume to be delivered display 38 and program infusion data display 40. Monitoring circuitry 41 is provided connected to the pump operation circuitry 43. The monitoring circuitry 41 may provide information for the program infusion display 40 and also for wireless transmission to the HIMS 60. The program infusion data display 40 may include capabilities for displaying entered data and for displaying current operational data. The current operational data display includes: nurse identification and/or number display 42, a unique patient identification name and/or number display 44, a drug name or other identification display 46, a dosage display 48, a rate display 50, a running time display 52, total volume of infusion display 54, current date display 101, current time display 103, current maximum dose limit 105, current minimum dose limit 107, current maximum rate 109, current minimum rate 111, current minimum volume to be infused 113, current maximum volume to be infused 115, patient weight 117 and patient height 119. Other displays such as alarm display 53 may also be included. For example, an alarm may be displayed at alarm display 53 upon detecting air in the line, upon detecting occlusion limits or upon detecting other conditions of which the operator may be notified. The monitoring circuitry 41 also provides the entered data and the current operating data to a wireless transmitter 45 for wireless transmission to an HIMS 60 (shown schematically as a remote computer terminal) including wireless receiver unit 61, a CPU 57 and display 55 such as a CRT screen. A data input unit 59, such as a keyboard, a mouse, or another data entry device may also be connected to the HIMS 60.

For purposes of operating the pump 10 according to the present invention, a power switch or power button 56 is provided on the control panel 22. A plurality of infusion data input controls 58, schematically represented as buttons 58, are also provided. The plurality of infusion data controls 58 may include input controls for manually entering rate, for entering volume to be delivered, for accessing a menu of drugs and options, and for toggling or otherwise selecting between various menu items, as well as for entering available menu items. These menu items will typically include available drug information, rates and dosage and other pump control information in order to effectuate programming of onboard pump control software or circuitry 43. Menu items may be selected using a toggle or other mechanism and may be appropriately entered into the pump control software or circuitry for operating the pumping mechanism.

With the understanding that any of a variety of possible types of IV pumps may be used in the present invention, the inventive wireless communication system according to one embodiment includes an IV pump 10 having pump operation circuitry 41 and circuitry 43 for monitoring pre-selected characteristics of pump operation. It will be understood from this disclosure, that the operation circuitry 41 and the monitoring circuitry 43 may be separate electrically connected circuitry or software or such circuitry may be integrally formed as unitary circuitry or software. The pump operational characteristics 15 such as parameters and states selected to be monitored, may be those that are specifically indicative of IV administration of medication to a patient 20. For example, characteristics of current infusion pumping operation may be selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, current maximum dose limit, current minimum dose limit, current maximum rate, current minimum rate, current minimum volume to be infused, current maximum volume to be infused patient weight and patient height.

A transmitter 45 is connected to the pump 10, as for example through the operation circuitry 41 and the monitoring circuitry 43, for transmitting a wireless pump signal 49 representing the pre-selected pump operation characteristics. The wireless pump transmitter 45 communicates with a hospital information management system (HIMS) 60. The HIMS 60 includes a receiver 61 connected to a receiver antenna 63 capable of receiving the pump signal 49 representing the pump operation characteristics. The HIMS also includes a computer processor 57 capable of storing and displaying the pump operation characteristics on a display 55 represented by the received wireless pump signal 49.

Another combination of elements is depicted in FIG. 2 to demonstrate an alternative embodiment, an IV medication infusion pump 10 is provided for use with a hospital information management system 60 (HIMS). A doctor's order transmitter 83 is provided that is capable of manually receiving an input doctor's order 82, as by a keyboard 85, for patient medication to be administered with an IV pump 10. The doctor's transmitter 83 is also capable of wirelessly transmitting a wireless signal 87 representing the input doctor's order 82. The hospital wireless communications system 9, having the IV pump 10 with wireless transmitter 45 and a receiver 61 at the HIMS 60 is thus expanded, according to this alternative embodiment, to receive a wireless signal 87 representing the doctor's order 82 for IV medication 17 for a patient 20. The doctor's order transmitter 83 provides a wireless signal representing the input doctor's order for patient medication that is to be administered intravenously, namely to be administered using the IV pump 10. In one such embodiment the doctor's order signal 87 is received at receiver 61 by the HIMS 60 for storage and/or for comparison to the actual operation characteristics, as represented by the signal 49 transmitted from the IV pump 10. The storage and comparison may be carried out using an appropriate CPU 57. The pump 10 may also be provided with wireless signal receiver 51 to receive the doctor's order wireless signal 87 directly. Alternatively, the HIMS may also be provided with a transmitter 65 to provide a HIMS wireless signal 67 to the IV pump 10, which signal 67 may include a retransmission of the doctor's order wireless signal 87, selected portions of the instructional content of the doctor's order 82, or other data or instructions such as instructions input at keyboard 59 or stored at CPU 57. The receiver at the IV pump 10 is capable of receiving such data or instructions for entry into the IV pump controls 43. At the pump the nurse or other health care professional will make data entry or instructions entry and pump activation according to appropriate safeguard, such as verification professional responsible for the particular hospital patient. Other possible components of the system 9 might also be capable of communication with the HIMS using wireless signals.

In another combination of elements demonstrating yet another alternative embodiment, a pharmacy receiver 88 may also be provided that is capable of receiving a wireless signal representing the doctor's order for medication. The wireless signals 87 may be communicated directly between the doctor transmitter 83 and a pharmacy receiver 88 or between the doctor transmitter 83 and the IV pump 10. The pharmacy receiver 88 may include a transceiver to communicate directly with the IV pump via wireless signal 91 or with the HIMS via wireless signal 89. The IV pump 10 may wirelessly communicate with the HIMS 60 and the HIMS 60 may wirelessly communicate with the IV pump 10, with the pharmacy 88, or with the doctor's transmitter 83.

In yet another alternative embodiment, all of the individual components wirelessly communicate with the HIMS 60 where the information may be re-transmitted to any of the other system components intended to receive the wireless signal representing selected information. In this alternative embodiment, the pharmacy receiver 88 includes apparatus 84, such as a computer terminal 84, for providing the order for patient medication in human readable form for the preparation of ordered patient medication for IV pump administration. The medication is provided by the pharmacist to a nurse' station according to the doctor's orders for proper administration to a patient receiving care from nurses who will be operating the IV pump. In this alternative embodiment, in addition to the wireless signal transmitter 45, the IV pump 10 also has a receiver 51 for receiving the wireless signal indicating the doctor's order. The signal indicating the doctor's order to the IV pump 10 may be a direct signal 87*i* from the doctor's order transmitter 83 or it may be a signal 91 from the pharmacy transmitter 88 or it may be a re-transmission signal 67 from the HIMS 60. In each case where a wireless signal transmitter and receiver is provided, there maybe separate transmitters and receivers electronically inter-connected, or there may be a combination transmitter and receiver unit known as a transceiver.

Figure 3:
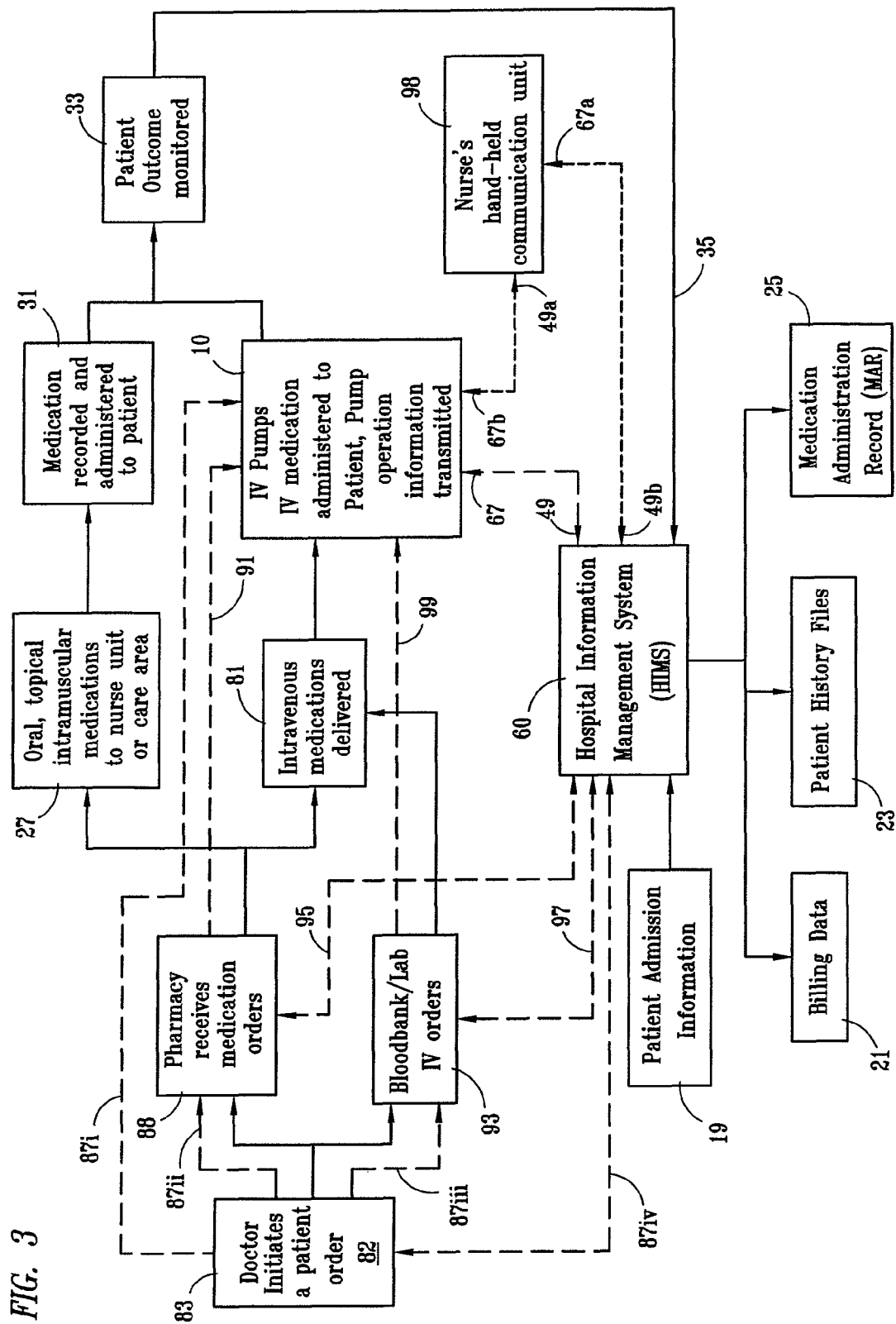
FIG. 3 is another schematic depiction of a wireless communication system from an IV pump to an HIMS and also depicting wireless communication among other elements of a hospital system including the IV pump and the HIMS.

Referring to the schematic flow diagram of FIG. 3, further combinations of inventive features may be understood. In this schematic the IV pump 10 for administering IV medication to a patient and for pump operation data transmission to a hospital information system HIMS 60, are depicted among other components in a flow diagram. Medication is ordered, prepared and delivered to a patient in a hospital or other institutional health care facility. The wireless communication signal 49 from the IV pump 10 to the HIMS 60 is depicted as dashed lines with the arrowhead directed toward the HIMS. The HIMS 60 might likewise communicate with the IV pump 10 along the dashed line as indicated by the arrowhead 67 pointing toward the IV pump. As will be discussed more fully below, the wireless communication between the IV pump 10 and the HIMS 60 might alternatively be in the form of a signal 49*a* from the IV pump 10 to a nurse's hand-held communication unit 98, and a retransmission signal 49*b* from the hand-held unit 98 to the HIMS 60, as depicted with dotted lines. Similarly, the HIMS 60 may communicate to the IV pump with a transmission signal 67*a* to the nurse's hand-held communication unit 98 (or a bedside terminal 98) and the retransmission signal 67*b* from the hand-held communication unit 98 to the IV pump 10. It may be understood that the doctor's transmitter and the nurses hand-held unit may be the same or similar type of wireless communication devices used for different purposes at different parts of the system by different professional healthcare givers.

To understand how the IV pump communication with HIMS operates within the entire IV medication delivery process and system 9, we may follow an example from a doctor's initiation of the patient order 82. This order 82 is communicated via wireless transmitter 83. A wireless signal from the doctor's transmitter 83 is received directly by the IV pump 10 as indicated by dashed line 87*i*. Alternatively, the doctor's order 82 may be wirelessly transmitted and received by the pharmacy transceiver 88, as indicated by dashed line signal 87*ii*. In the case where the doctor's order requires blood products or other laboratory prepared IV solutions, the doctor's order may be transmitted to and received by a laboratory or a blood bank receiver or transceiver 93 via wireless signal 87*iii*. Alternatively, the doctor's transmitter 83 may provide a signal 87*iv* to be received by the HIMS transceiver 61. The HIMS may be used to re-transmit the doctor's order with or without appropriate modifications such as additional instructional information to the pharmacy via wireless signal 95 or to the laboratory 93 via wireless signal 97. The pharmacy 88 (or other healthcare professional) or the lab 93 (or blood bank) may be provided with a transceiver such that medication orders received in the pharmacy 88 or received in the lab 93, whether received from the HIMS or from the doctor's order transmitter 83 or otherwise, may be then appropriately prepared for administration to the intended and properly identified patient 20. The doctor's order 82 may be transmitted via a wireless signal 87*i* to the IV pump 10, with or without additional instructions from the pharmacy 88 or the lab 93 as appropriate for a particular medication preparation or for a particular patient. Such additional instructions may be transmitted to the IV pump 10 via a wireless signal 91, in the case of the pharmacy, and via wireless signal 99, in the case of the lab. The prepared medication or the prepared blood product or other laboratory IV solution container is then physically provided to the nurse's station 27 (or care area 27) for delivery to the pumping unit 10 at the patient's hospital room, as indicated by the solid line and direction arrow head to block 81 in FIG. 3. The prepared IV medication container or prepared blood product container 12 is then appropriately attached to the IV pump 10. The IV pump 10 would therefore receive a wireless signal indicating the appropriate instruction pumping characteristics for the IV fluid container that is connected to the IV pump 10 for the identified patient 20. Such infusion data and pumping characteristics will be validated by a nurse or another system of validation or verification will be used, in order to maintain the integrity of the system. For example, in the case of validation by the nurse, the nurse enters, or scans, the information from the IV fluid container identifying the medication, identifies identify the patient, and provides the nurse's identification consistent with authorization to administer medications to the patient. The pump operation data is downloaded from the doctor's order, from the pharmacy instructions or from the HIMS 60. For purposes of central administration control, the doctor's order and/or the pharmacy instructions may be wirelessly received at the HIMS and such order and instructions checked and corroborated with patient information and/or medical information stored in the HIMS to confirm proper administration to the correct patient. In that embodiment, the nurse may activate wireless downloading of pump operation data from the HIMS 60 to IV pump 10, as, for example, by wireless signal 67.

It will be noted in FIG. 3 that the inventive wireless IV pump system works with, and as a compliment to, other health-care services provided to the patient and managed with a hospital information management system. For example, the patient admissions information 19 may be provided directly to the HIMS. Also, where the pharmacy prepares oral, topical or intramuscular medications, those medications may be delivered to a nurse's station as indicated by solid arrow to block 27 and the oral, topical or intramuscular medication may be recorded and administered to the patient as indicated by solid arrow to block 31. The patient outcome may be further monitored appropriately as with a patient's written chart 33 and that information may be conveyed to the HIMS, as indicated by arrow 35. In this manner, the HIMS 60 may receive information from any combination of various elements, or from all of the various elements of the patient health-care system 9. The information may be appropriately used in providing billing data at block 21, in providing a patient history file at block 23 and/or in providing a medication administration record (MAR) at block 25.

In FIG. 3 a nurse's hand-held communication unit 98 or a bedside terminal 98 is also shown, for purposes of indicating yet another alternative embodiment of the system. Additional aspects of this alternative embodiment may also be understood, with reference also to FIG. 4. The nurse may use a hand-held or bedside communication unit 98 to manually enter information from a label on an IV container. The nurse may transmit the instructional data to the IV pump and upon confirming that the patient, medication and pumping data match, the nurse may initiate IV pumping. Alternatively, a hand-held or bedside communication unit 98 specially adapted with bar code reading capabilities may be used to scan bar code information from an IV container. Further alternatively, the nurse may receive a pharmacy medication instruction signal wirelessly and/or a doctor's order signal wirelessly, by which the patient medication can be compared to the label on the physical IV container of fluid. As a further alternative, the nurse may enter an appropriate patient and IV medication identification into the hand-held communications unit 98 and this identification may be wirelessly transmitted to the HIMS as an access code. With the appropriate identification information the nurse can receive appropriate information and instructions from the HIMS for IV pump administration of the identified IV medication to the identified patient. Those pump characteristics may be transmitted to the hand-held unit via signal 67*a* and retransmitted to the IV pump from the hand-held communications unit via wireless signal 67*b*. Again upon confirming the information loaded into the IV pump, the nurse may activate pumping operations.

The hand-held or bedside communications unit 98 can similarly be used by the nurse to receive a wireless signal from the IV pump, indicating the IV pump operation characteristics at any point in time. The nurse may choose to poll any given IV pump as by using individual pump identification codes or addresses. Alternatively, the entire operations log for IV pump operation characteristics over a period of time might be uploaded to the handheld or bedside unit 98 on the command of the nurse. The pump operation characteristics, received by wireless signal 49*a*, can then be retransmitted to the HIMS as by a wireless signal 49*b*.

Figure 4:
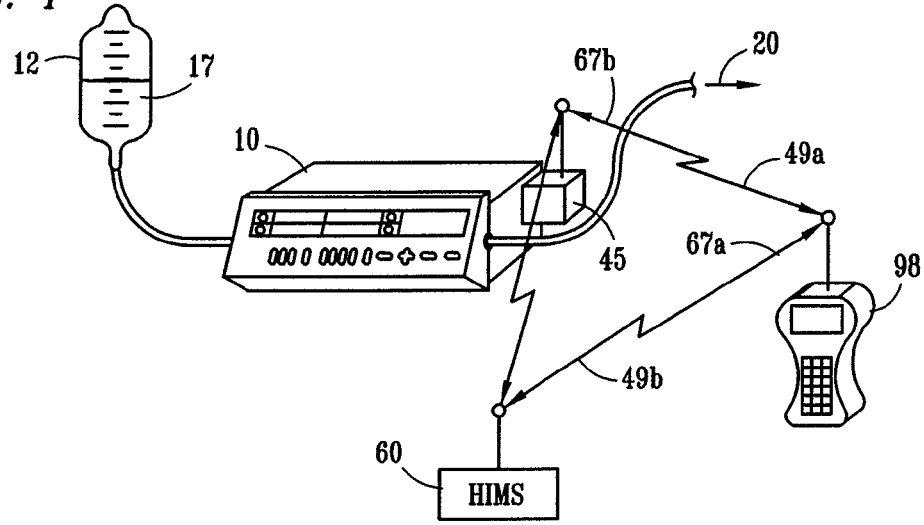
FIG. 4 is an alternative embodiment of the wireless communication system for IV pump and HIMS with an intermediary hand held transceiver.

This alternative embodiment may be more fully understood with reference to FIG. 4 in which only the nurse's hand-held or bedside communication unit 98, the HIMS 60 and the IV pump 10 are depicted as an alternative inventive subcombination of the invention. In this subcombination, the information from the IV pump is transmitted via wireless signal 49*a* and is received by the hand-held unit 98. The information may be displayed to the nurse and the nurse may retransmit the received information via signal 49*b* to the HIMS 60. Similarly, the nurse may wish to compare the current pump operation characteristics 15, represented and received as wireless signal 49*a*, with the desired pump operation characteristics received from the HIMS. The nurse may do this by way of activating and receiving a wireless signal 67*a* from the HIMS to the hand-held or bedside unit 98. Thus in certain appropriate situations, the HIMS operational instructions, represented by signal 67*a*, may be transmitted by the hand-held unit activated by the nurse as a wireless signal 67*b* to the IV pump 10. Where a plurality of IV pumps 10, 10*b*, 10*c*, 10*d*, and 10*z* are present, the pump identification codes may be used to access only the desired pump. The IV pump identification code can be readable from the pump itself so that there is no doubt that the proper pump at the identified patient's bedside is being accessed and/or programmed for infusion operation by the nurse.

Figure 5:
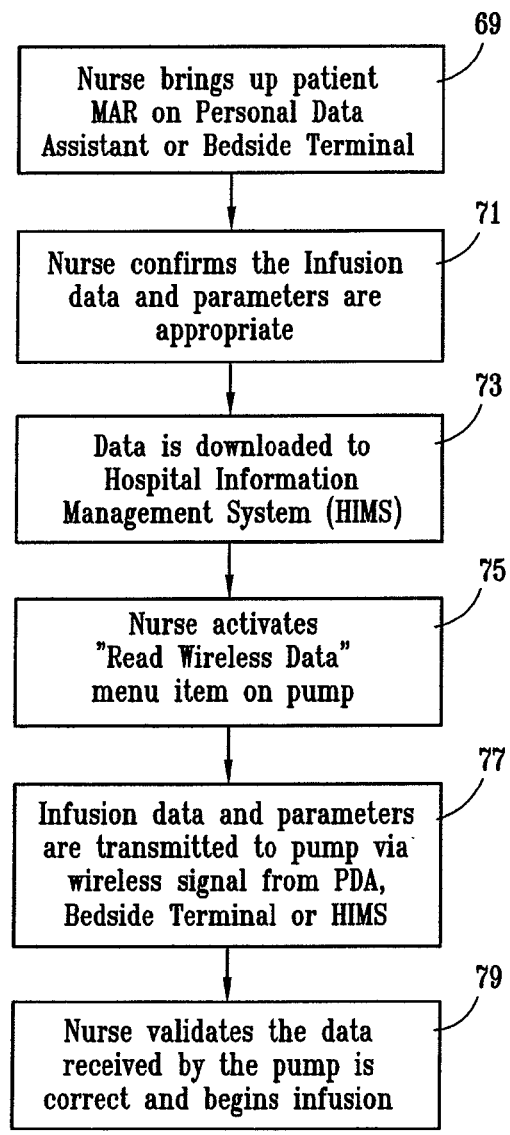
FIG. 5 is a schematic flow diagram demonstrating use of a wireless communication system at the pump according to one aspect of the present hospital system and IV pump wireless communication system.

FIG. 5 schematically depicts an enhanced security operating sequence for operating an IV pump with wireless signal transmitter 10 as well as the nurse's hand-held or bedside wireless signal transmitter 98. In this method, a nurse brings up a patient's medication administration record (MAR) on the hand-held unit 98 at step 69. The nurse then confirms that the infusion data and IV pump operating characteristics are appropriate for the MAR information for the identified patient at step 71. Where the characteristics are appropriate, data is communicated to the HIMS at step 73 and the nurse activates the read-wireless data menu on the IV pump at step 75. With the read-wireless data menu item activated, the infusion data and characteristics are transmitted to the pump via wireless signal, according to step 77 in FIG. 5. With the infusion pump characteristics thus entered wirelessly into the infusion pump, the nurse may validate that the data received by the IV pump is correct. For example the correct information is observed by the nurse on the pump display 40 before the nurse activates the pump. Upon validating the accuracy of the entry, the beginning of infusion may be authorized at step 79.

In the embodiments depicted the IV pump has a transmitter (or transceiver) for transmitting a wireless signal to the HIMS. The transmitter is operatively connected to certain pump operation circuitry for monitoring pre-selected pump operations and for transmitting a wireless signal representing such pre-selected pump operational characteristics indicative of IV administration of the patient medication to a patient. The HIMS is provided with a wireless signal receiver (or transceiver) capable of receiving the signals from the IV pump transmitter.

While the IV pump 10 is operating, the operational characteristics 15 of the pump may be monitored with appropriately connected circuitry, software or a combination of circuitry and software all referred to herein as circuitry 41. The monitoring may be done continuously, at regular intervals, at predetermined irregular intervals, or upon the occurrence of predetermined events, or upon the occurrence of any event that changes the state of the pump. By way of example, such state change events could include starting or stopping, changing of infusion rate, activation of an alarm, or approaching a predetermined time in advance of an anticipated event. The pump operation information is transmitted by the wireless pump transmitter and to the HIMS wireless signal receiver. HIMS programs or circuitry may perform function such as information acceptance, storage, comparison and/or other manipulation of the information. Information that is wirelessly transmitted to the HIMS by the pump transmitter may include other information such as medication name, patient ID, and nurse ID when available in addition to operational characteristics. Also, pump alarm conditions, malfunction conditions, and maintenance conditions may be transmitted.

End of infusion warnings may be usefully signaled according to one alternative inventive aspect of the invention. For certain types of medication, such as antibiotics, causative medications, vasoactive medications and anti-blood clotting medications, the end of infusion warnings may be usefully programmed into the HIMS, or may be made programmable, to occur with sufficient lead time for the HIMS to "notify" a healthcare professional (as for example with a wireless signal to the pharmacy terminal) so that the healthcare professional can to prepare the next medical solution and have it delivered to the patient's IV pump before the current bag is completely emptied. Other information such as administrative information including for example specific pump ID, pump location and hours of operation, and any maintenance reports may also be transmitted to the HIMS via wireless signal transmission. For example, spaced apart HIMS receiver nodes with known locations may be placed throughout the hospital or health care facility. Such HIMS receiver nodes may receive signals from a plurality of separate IV pumps and by using pump ID codes, signal strength and/or signal direction detection means, the location of each of the plurality of separate IV pumps within the facility may be determined.

In one embodiment the pump may also be capable of downloading the pump operation log (Op log). For example, the Op log may be transmitted to the HIMS at each nurse shift change, at regular timed intervals, or upon receipt of a HIMS inquiry signal transmitted to the IV pump. In such an embodiment the Op log is separate from the current real time pump operation information that is transmitted to the HIMS.

Wireless communication between the doctor's order transmitter 83, the pharmacy transmitter 88, and the IV pump transmitter 45 or between any combination or from all of the components may also facilitate medical administration to a patient in a hospital or other institution or health-care facility.

A computer processor 57 of the HIMS 60, that is capable of storing the information represented by the received signals, may be provided. The HIMS 60 may also include software or circuitry that is capable of comparing doctor's order for patient medication with pharmacy instructions and/or capable of comparing the doctor's order or the pharmacy instructions with the wirelessly transmitted IV pump characteristics that are indicative of the actual delivery of medication to the patient. The HIMS may be programmed for comparing the doctor's order to the actual pump operation delivery characteristics. The comparison may for example, confirm successful doctor ordered delivery or it might determine that delivery was not initiated or completed as instructed. According to yet another alternative configuration of the invention, the HIMS will be able to display, in human readable form, the order, the pump operation characteristics and the results of the comparison indicative of successful completion of administration of this ordered medication to the patient or otherwise. The HIMS can be useful to communicate the information to billing at 21, to patient history files at 23, and to a medication administration record (MAR) at 25 for monitoring safe and secure records of medications, especially controlled substances. In yet other possible combinations with the present invention the type of blood product to be infused might be compared to patient blood type information in the HIMS or patient allergies to medications to be infused might be compared to HIMS records for the patient.

In yet another embodiment the pharmacist's instructions in bar code format may be scanned into the IV pump from a bar coded IV bag, bottle, syringe or other container labeled by the pharmacist or healthcare professional and scanned with a bar code scanner connected with the IV pump. An authorized nurse or other authorized healthcare professional may selectively activate the bar code scanning capability. Upon activation, the nurse is prompted to scan a nurse's ID, which ID includes a special authorized user code. If the authorization code is present, then the pump prompts the nurse to scan in the patient's ID. When the patient ID is properly scanned, then the nurse is prompted to scan information from the pharmaceutical fluid container, whether a bag, a bottle, a syringe or another container. Upon reading information from the label of the container of medicinal fluid, pump control software displays an appropriate display of the name of the drug identified by the bar code label. The software may further capture the drug name, the concentration, concentration volume, volume to be delivered, minimum dosage limit, maximum dosage limit and infusion rate, if not calculated. All of these operation characteristics might be selected for wireless transmission to the HIMS. If the nurse validates all of the required infusion information, the infusion may be initiated according to the accurately scanned infusion information. The infusion information may include the volume to be delivered and infusion rate that is read directly from the infusion information bar code label on the fluid container and into a control program of the infusion pump. If any of the required information cannot be accurately validated by the nurse, then the scan mode is exited and the nurse manually inputs the required data and infusion rates into the pump software control program using control panel buttons, toggles and displays. Any portion or all of the current pump operation activity may be transmitted wirelessly to the HIMS or it may be stored in a pump operation log that may subsequently be transmitted via wireless signal to a data collection terminal, to the HIMS or to both. Any or all of this information might be selected for transmission to the HIMS for storage or for comparison to the doctor's order. If there is a mismatch, an alarm or warning might be issued to the appropriate personnel or directly to the IV pump.

According to the alternative embodiment shown in phantom lines at 62 and 64 in FIG. 2, the pump housing 11 also carries an operationally connected bar code scanner 62. The barcode scanner 62 is depicted having a scanner window 64 on the side of the pumping housing 11. It will be understood that the scanner window 64 might also be in another position or might be otherwise directed for usefulness of the pump. In the embodiment depicted and where a plurality of pumps 10 might be stacked one on top of the other, attached through pole clamps 28 to a pole 29, it is useful to provide the scanning window 64 facing toward a side or toward the front. The side is a particularly useful position for the bar code scanning window 64 because it is conveniently accessible and permits effective use of the front panel 22 for display and manual programming.

The bar code scanner 62 is useful with a container 12, that has been prepared by a pharmacist with therapeutic fluids 70 therein and a barcode label 66 thereon. The container 12 is provided with a bar code label 66 and may also include a human readable printed infusion data label 68 corresponding to prescribed drug, dosage, rates, limits, and patient information. The operator may activate the scanning mode of the infusion pump by using menu and cursor keys to activate a menu item. The pump prompts the user to provide certain required security information, such as including a scan of a nurse's ID badge or card. A nurse's ID badge may have a unique identification code number as an appropriate authorization code. Only with the nurse's ID badge can the scanning mode be continued. Subsequent to scanning in the nurse's ID, a unique patient ID may be scanned, as from a patient wristband or a patient ID card, having a bar code to uniquely identify the patient by name and/or by patient number. After the nurse's ID and the patient's ID are appropriately scanned and confirmed, as by using the "E" or "enter" button 100 or other appropriate confirmation, then the bar code label 66 of the medication container 12 can also be scanned. The pharmacist, who prepares the medication 17, places the bar code label on the medication container 12. The infusion information may include the unique patient identification field 72, the drug name or identification 74, a dosage 76, a rate 78 and other infusion information 80, as may be appropriate. For purposes of further confirmation, all the requisite information may also be printed in a human readable label 68 corresponding to the bar code fields that are scanned for convenient and accurate entry and then manually confirmed with reference to the printed human readable information.

Figure 6A:
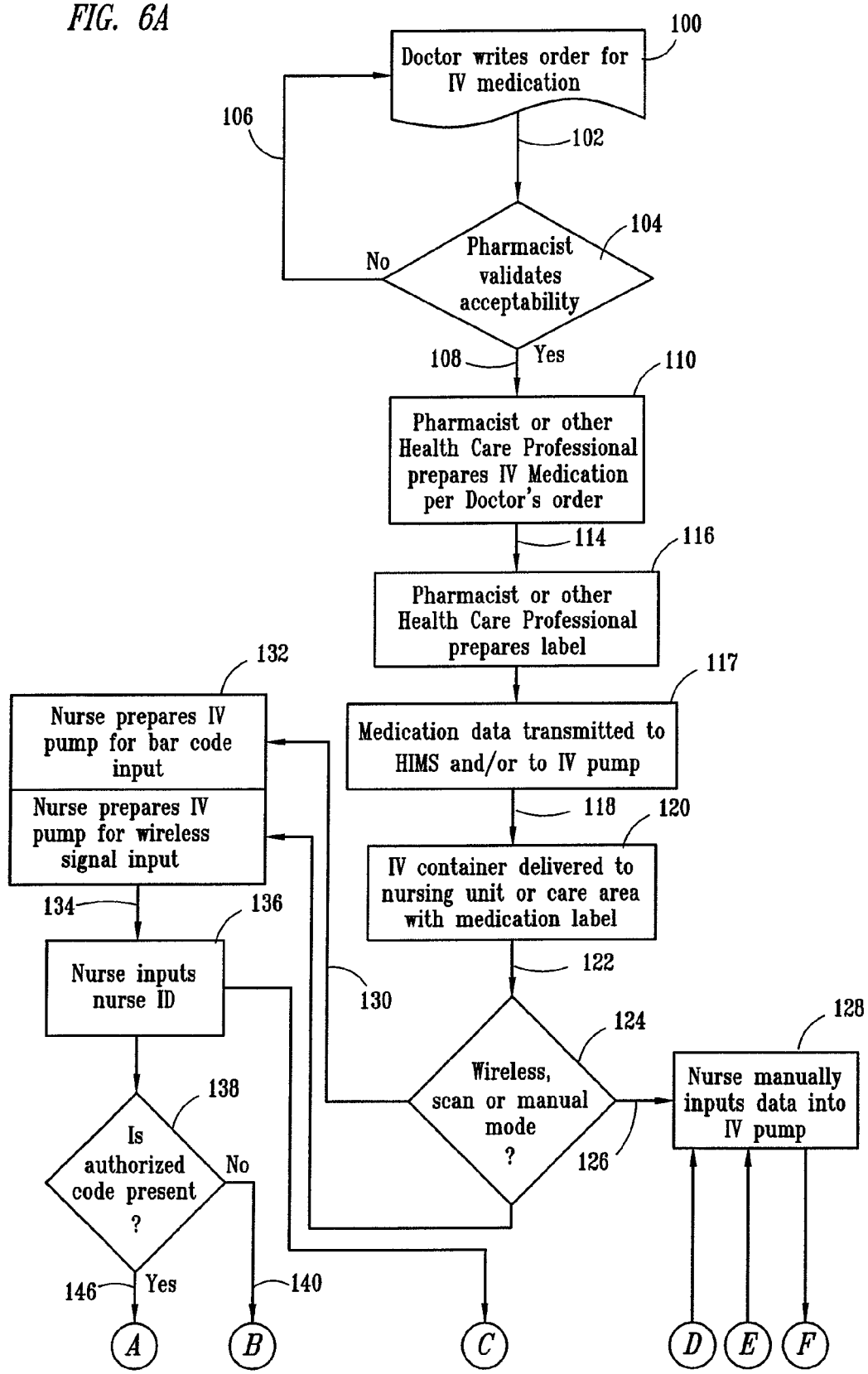
FIG. 6, including FIG. 6A continued on FIG. 6B, is a schematic flow diagram further depicting a wireless communication IV pump and HIMS system further including a bar code reader for entry of IV medication pumping information into the IV pump according to an alternative embodiment incorporating certain aspects of the invention.
Figure 6B:
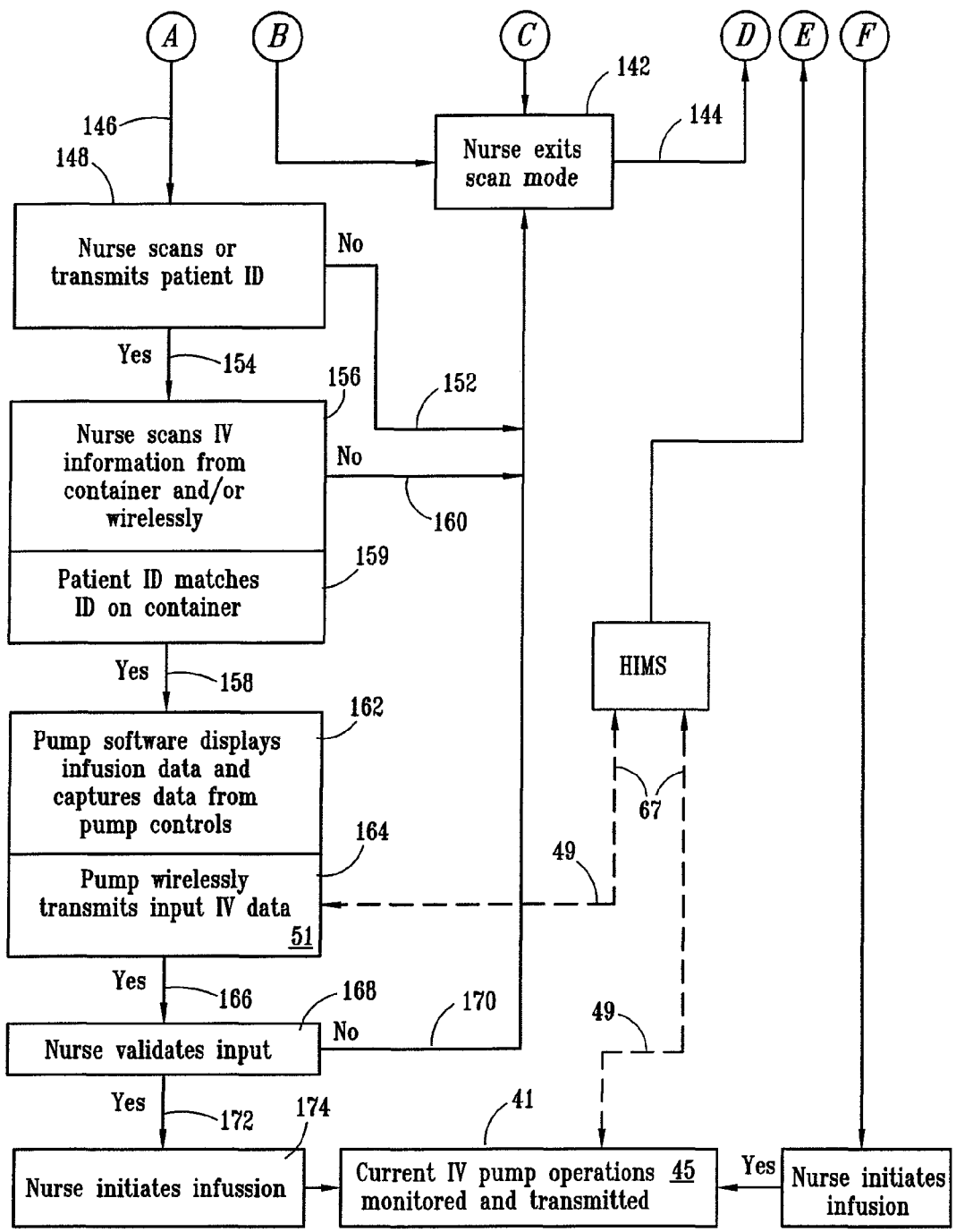

FIG. 6 is a schematic flow diagram of the operation of one alternative embodiment of a wireless signal transmitter pump in a system for improved accuracy and security using wireless signal transmission to a HIMS. In this flow diagram, the initial step is for the doctor to make an order for medication as at step 100. The order for the medication goes to a qualified pharmacist and, in particular, a pharmacist who prepares medications for the institution at which the infusion will be administered as indicated by arrow 102. In step 104 the pharmacist receives the order and validates the acceptability of the medication ordered for a particular patient. If, for any of a number of reasons, the pharmacist believes that the medication is not acceptably written by the doctor, then the pharmacist sends the order back to the doctor, as indicated by arrow 106, so that the order may be rewritten to be acceptable to the pharmacist. In the event that the order is acceptable, then the pharmacist moves to the next step, as indicated by arrow 108, to step 110 for the preparation of the medication according to the doctor's written order. Immediately upon preparing the medication per the doctor's order, the pharmacist goes to the next step, as indicated by process arrow 112, to step 114, where the pharmacist prepares a label 116 for the medication. With additional information available to the pharmacist through the healthcare facility's admission records as stored in the HIMS, the prepared labels may also include the patient's name, the patient's identification number, as assigned in the admissions procedure. The label includes the drug name, according to the preparation made by the pharmacist, the concentration, the concentration volume, the volume to be delivered and the infusion rate, if not calculated. The patient's height and weight may also be provided or other appropriate infusion data, if it is applicable to the therapy anticipated by the infusion. Referring again to FIG. 2, the pharmacist may be provided with a wireless transmitter 88 connected to an input 91 and keyboard 93 terminal by which the information for the medication is entered into the terminal 91 and transmitted via transmitter 88 to the HIMS 60 receiver 61. The pharmacist may prepare human readable labels and may also be provided with bar code specifications, to provide labels bar code readable by the infusion pump.

The pharmacist then releases the container 12 of the medication 70 and transmits the medication data to the HIMS. The medication itself is then delivered at 118 to a nursing unit appropriately assigned to the identified patient 20, as indicated at step 120. The assigned nurse or other authorized healthcare professional then carries the medication container 12 to the patient's room, bedside and infusion pump where the medication data including pump operating instructions are input into the pump control circuitry, as indicated by arrow 122. The nurse or other authorized healthcare professional might scan the infusion information into the pump where a bar code scanner is available, or might input the infusion data manually, or might activate wirelessly transmission of IV information to the IV pump as indicated by decision box 124. The pharmacist may wirelessly transmit the medical information to the HIMS. In the embodiment where the IV pump is also provided with a wireless receiver (or a transceiver), the data may be transmitted to the IV pump directly from the doctor, the pharmacist, the HIMS or from the nurse's handheld communication unit. This provides the healthcare institution with the options to instruct authorized personnel to input the data manually, to provide bar code labels to allow the data to be scanned in for improved administration capabilities provided by the bar code scanner or to download the medication instructions from the HIMS. In any event, the nurse validates the input data as it is displayed at the pump before initiating the infusion.

The healthcare institution may phase in the use of the wireless pump communication capabilities, or alternatively, may determine appropriate criteria for internal purposes for wireless transmission of certain types of infusion medications, scanning other types of data and/or manually inputting other data. If the manual input mode is selected as indicated by arrow 126, then the nurse enters the infusion data from the control panel 22, as indicated by action block 128. When the automatic infusion data entry is determined to be appropriate, as indicated by arrow 130, the nurse then prepares the pump for input data or for wireless transmission input, as indicated at step 132.

In one alternative embodiment, the infusion pump 10 may be provided with recording capabilities in addition to the wireless transmission capabilities. For example, a computer chip memory may be provided so that appropriate infusion data is recorded in an operation log (Op log). The Op log can be reviewed for administration purposes, for quality control purposes and, importantly, for purposes of the physician's review to determine appropriate continued or future treatment or medications for the patient. The recorded pump information may be wirelessly transmitted to HIMS.

Preparation of the pump for bar code input or wireless input includes not only turning the pump on, as with a power button 56, but also setting the pump for the automatic bar code scanning mode or wireless receiving mode. This may be done from a menu or otherwise depending upon the pump controls. When the pump is in the scan mode, as indicated by arrow 134, the nurse is prompted to scan in a nurse's ID. A printed bar code on an ID tag can be used for this purpose. (The barcode ID is also made with a compatible bar code labeling system for use with the bar code module used in the device). To facilitate system security, all authorized healthcare professionals employed by the healthcare facility with qualifications for establishing an infusion to a patient, are provided with an identification tag, badge, card or other coded identifier having a specialized authorization code. If the authorization code is present, the automatic bar code scanner may be initialized for establishing infusion data for a patient, as indicated by block 138. If the authorization code is not present or if the nurse does not scan in an appropriate ID, then the automatic system requires the nurse to exit the scan mode, as indicated by arrow 140. If infusion continues to be desired after the scan mode is exited at block 142, a the manual input mode may be initiated, as indicated by arrow 144 leading to the manual mode entry block 128. Alternatively, the operator could start over with the scan mode initialization at decision block 124.

If the nurse's ID is properly entered at 136 and if the authorization code is present in the entered ID, as indicated by 138, then the control software allows the nurse to proceed, as indicated by arrow 146. The nurse is prompted to scan in the patient's ID, at step 148. The patient's ID may appropriately be established with the patient's ID set forth on a wristband having a bar code thereon. In certain situations, the patient's care may limit the availability of using the wrist band for scanning purposes and the patient's ID may be scanned from a patient card, a patient badge, or the patient's chart, or other bedside available bar code so that proper patient identification is securely established. According to a an optional security check, a patient ID is to be scanned in order for the automatic bar code scanning mode to continue. If the patient's ID is not scanned, as indicated by arrow 152, the nurse is then returned to decide whether to manually input the data into the pump, as at decision block 142 and manual input block 128, as described above.

If the patient ID is scanned, as indicated with arrow 154, the nurse will be prompted to either, scan in the infusion information from the container, as set forth in action block 156, or receive a wireless signal from the HIMS. The scanning of the information from the container would involve scanning the bag, bottle, syringe or other medication container past the bar code scanner window 64 with an appropriate confirmation that the scanning was completed, as by an audible sound signal, a visual signal or both. If the container information were readably scanned from the container, then the process would move forward, as indicated by arrow 158. If not, then, as indicated by return arrow 160, the nurse would be again returned to decision block 142 and manual input action block 128.

In the event that all the infusion data can be appropriately validated by the nurse or healthcare professional at the pump, as set forth in step 168. If the nurse cannot validate the input or any aspect of the input, then the system returns the nurse, as indicated by line 170, to exit the scan mode at 142 and to either move to the manual input 128 or otherwise correct the situation. Assuming the nurse can validate the accuracy of all the required input data that is downloaded, then the nurse initiates the infusion, as indicated by arrow 172 and action step 174.

Figure 7:
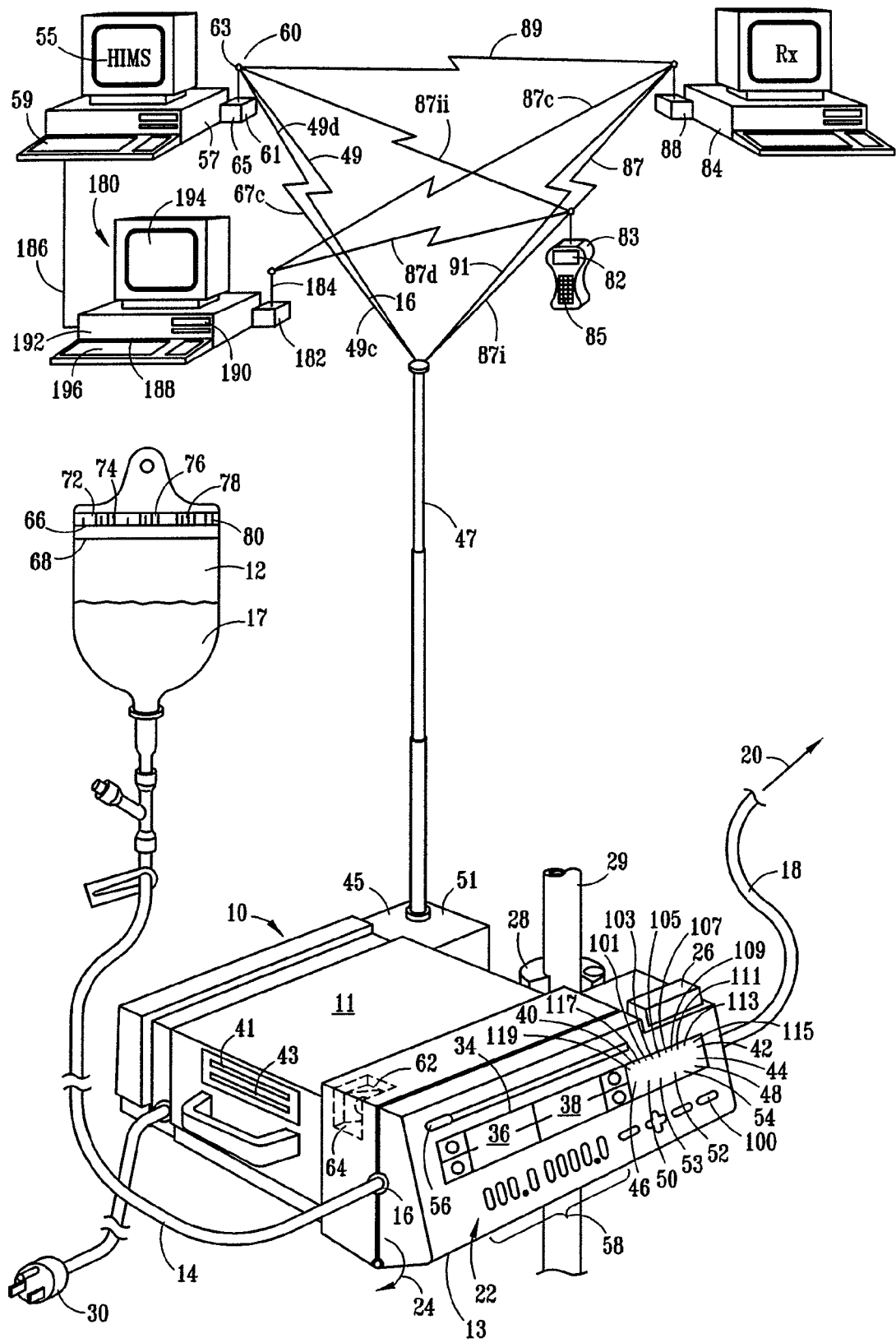
FIG. 7 is a schematic perspective view of an alternative embodiment of an infusion pump having a wireless signal transceiver and a system having a data collection terminal.

Yet another alternative embodiment is depicted in FIG. 7. A wireless communication pump 10 and a system, with all the alternative embodiments as described in connection with FIG. 2 above, is further provided with one or more data collection terminals 180. The data collection terminal 180 is capable of receiving instructional data from the HIMS 60 and is capable of receiving real time pump operational information wirelessly as a signal 49 from pump 10. The instructional data may be received either as a wireless signal 67c from the HIMS transmitter 61 with a wireless signal receiver 182 and an antenna 184, or the instructional data maybe received in the data collection terminal 180 through a hard wire connection 186. The real time pump operational information for any particular pump 10a. 10b, . . . and 10z is received by a wireless signal 49a, 49b . . . and 49z from that particular pump 10a, 10b . . . and 10z. The data collection terminal 180 is provided with a computer processor unit 188, information storage capabilities 190, information access and retrieval capabilities 192, and information display capabilities 194. For example, a personal computer processor unit 188 having a disc storage unit 190, a computer program 192 for accessing the storage unit and retrieving desired information for display on a CRT display monitor 194. The computer 188 maybe connected to a wireless signal transceiver either digitally or through an analog to digital converter. The wireless signal transceiver receives instructional data signals from the HIMS 60 and also receives real time pump operation signals from the pump 10. The instructional data and the real time information signals are received, converted to digital information streams if necessary and then stored according to the computer program. A user interface 196, such as a keyboard, is provided by which the operator can interface with the computer program to access stored data or information, to display such information or data on the monitor 194, to transmit such information or data to the HIMS 60 or to a selected pump 10*a*, 10*b*, . . . or 10*z*, to transmit such information or data to another terminal, to transmit such information or data to the pharmacy terminal 84, to communicate such information or data with other devices or any combination of the above.

Figure 8:
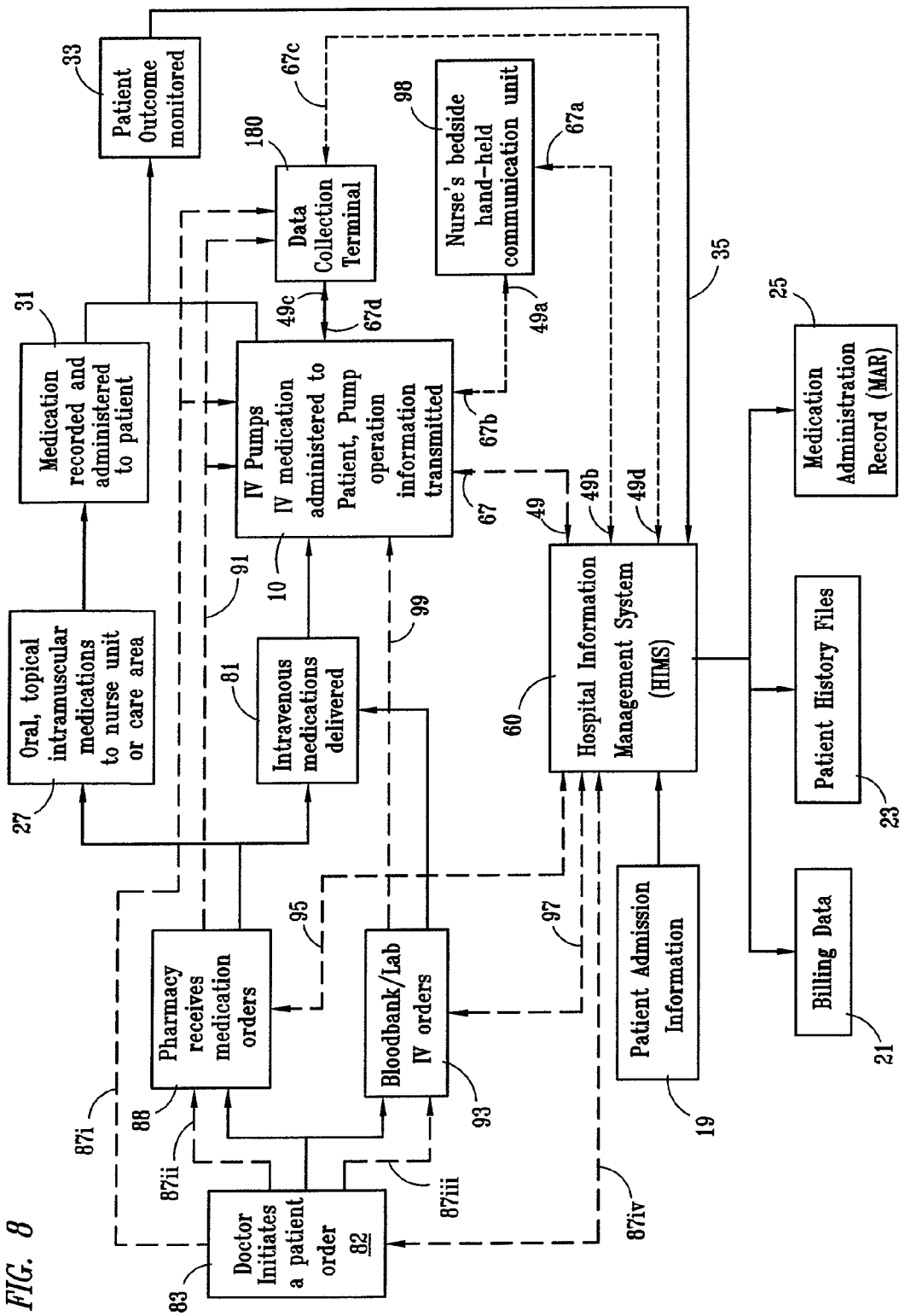
FIG. 8 is schematic depiction of the wireless communication system of FIG. 7 depicting wireless communication among elements the system including the IV pump, the HIMS, the pharmacist terminal, a handheld terminal or bedside terminal and a data collection terminal.

The alternative embodiment depicted in FIG. 7 is included in the schematic diagram of FIG. 8. With reference to FIGS. 7 and 8 together, additional aspects of this alternative embodiment may be further understood. The operator whether a nurse, a doctor or other authorized healthcare professional may use the data collection terminal 180 to access information transmitted to, or transmitted from, an IV pump 10. The operator may access the current real time operational characteristics and may also access the instructional data transmitted to the IV pump. The data collection terminal 180 can be programmed to collect real-time data on a periodic basis and to store a log of the information for any or all of several selected pumps. The data collection terminal may receive pharmacy medication instruction signals 87*c* wirelessly and/or a doctor's order signal wirelessly, and bar code entered medication instructions comprising current pump operation characteristics can be compared at the data collection terminal. With the appropriate identification information the authorized operator can receive appropriate information and instructions from the HIMS for IV pump administration of an identified IV medication to an identified patient. Those pump characteristics may be transmitted to the data collection terminal and retransmitted to the IV pump. Again, the doctor, nurse or other authorized healthcare professional will only activate pumping operations upon confirming that the information loaded into the IV pump is correct.

The data collection terminal 180 can similarly be used by the operator to receive a wireless signal from the IV pump, indicating the IV pump operation characteristics at any point in time. The operator may choose to poll any given IV pump as by using individual pump identification codes or addresses. Alternatively, entire operations log for IV pump operation characteristics over a period of time might be collected and stored at the data collection terminal. Where such a log is stored at the pump, the op-log may be periodically uploaded to the data collection terminal at programmed intervals of time or on the command of the operator. The pump operation characteristics, received by wireless signal 49*a*, can then be retransmitted to the HIMS as by a wireless signal 49*b* from the data collection terminal.

In large facilities a plurality of data collection terminals may be located at a plurality of convenient locations for access and monitoring as for example at each of the nurses stations in a large hospital for data collection from the IV pumps for which the nurses of that station are responsible. The information from each IV pump is transmitted via wireless signal 49*a* and is received by the data collection terminal. The information may be displayed to the nurse and the nurse may retransmit the received information via signal 49*b* to the HIMS 60. Similarly, the nurse may wish to compare the current pump operation characteristics 15, represented and received as wireless signal 49*a*, with the desired pump operation characteristics received at the data collection terminal 180 from the HIMS 60. The nurse may do this by way of activating and receiving a wireless signal 67*a* from the HIMS to the data collection terminal 180. Thus in certain appropriate situations, the HIMS operational instructions, represented by signal 67*a*, may be transmitted by the data collection terminal 180 activated by the nurse as a wireless signal 67*b* to the IV pump 10. Where a plurality of IV pumps 10, 10*b*, 10 *c*, 10*d*, and . . . 10*z* are present, the pump identification codes may be used to access only the desired pump. The IV pump identification code can be readable from the pump itself so that there is no doubt that the proper pump at the identified patient's bedside is being accessed and/or programmed for infusion operation by the nurse.

A wireless communication system from an IV medication infusion pump to a hospital information management system (HIMS) is provided including a medication order transmitter capable of receiving input of a doctor's order for patient medication to be administered with an IV pump. The IV pump is uniquely capable of wireless transmission of a first signal representing the input doctor's order for patient medication that is to be administered intravenously, namely using the IV pump. A pharmacist receiver is provided that is capable of receiving the first signal representing the doctor's order for medication and having circuitry for providing the order for patient medication in human readable form for the preparation of ordered patient medication for IV pump administration. The medication according to the doctor's orders as may be enhanced or supplemented by the pharmacist for proper administration to the patient are provided to the IV pump. The IV pump having a receiver for receiving the first signal indicating the doctor's order, also has a transmitter for transmitting a wireless signal that might be designated a second wireless signal. The transmitter is operatively connected to certain pump operation circuitry for monitoring pre-selected pump operations and for transmitting such a second wireless signal representing pre-selected pump operation characteristics indicative of IV administration of the patient medication to a patient. A hospital information management system is provided with a signal receiver capable of receiving the first and second signals. A computer component of the HIMS that is capable of storing the information represented by the received signals is also provided with software or circuitry that is capable of comparing doctor's order for patient medication with the IV pump characteristics indicative of delivery of medication to the patient. The HIMS is thus programmed for comparing the doctor's order to the actual pump operation delivery characteristics. The comparison may for example, confirm successful doctor ordered delivery or it might determine that delivery was not completed as instructed. The HIMS will be able to display the order, the pump operation characteristics and the results of the comparison indicative of successful completion of administration of said ordered medication to said patient or otherwise.

In one embodiment the pumping instructions in bar code format may be scanned into the IV pump from a bar coded IV bag, bottle, syringe or other container labeled by the pharmacist and scanned with a bar code scanner connected with the IV pump.

Thus, what has been disclosed is a system and medical infusion pump with bar code reading and wireless communication capabilities, to provide pump operation characteristics to or from an HIMS in a hospital or other healthcare institution or facility. The medical infusion pump capable of wireless signal transmissions of pump operation characteristics and/or signal reception of pump operation instructions and the HIMS capable of receiving, transmitting, storing and displaying information derived from the operation characteristics also forms a part of a patient care system. The patient care system provides for an authorized pharmacist or health care professional to prepare and label infusion fluids including medicines, drugs, and other pharmacological infusion products to be infused to patients upon doctor's orders. The labeling information may include patient ID, patient height, patient weight, drug information and drug administration dosage, minimum dosage limits, maximum dosage limits and rate information. The patient's doctor orders medicines directly from the pharmacist and the pharmacist prepares the infusion fluid and labels the container from which the fluid will be infused to the patient. The pump is provided with operation parameter monitoring circuitry connected to a wireless transmitter, by which the characteristics are transmitted to the HIMS. The authorized healthcare professional such as the nurse may scan in their own personal ID as an authorization code to indicate their authorization to administer medicines to the patient. The authorized user confirms the accuracy of the pump operational instructions prior to administration of the medicine to the patient. Thus only an authorized healthcare giver such as an identified nurse is permitted to activate the pump for operating according to information loaded into the pump control circuitry or software after confirming that the patient information as well as the drug administration information as it is displayed at the pump. In any event whether the IV pump is instructed to operate wirelessly, with a bar code scanner, manually or otherwise, the wireless transmission of IV pump operation characteristics to the HIMS is useful to the patient and to the hospital for increasing the security, efficiency and effectiveness of health care provided to patients requiring IV medications and treatments.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A wireless communication system from an IV medication infusion pump to a hospital information management system (HIMS) comprising:
   (a) pump operation circuitry in said IV medication infusion pump for operating said IV medication infusion pump and for continuously monitoring pre-selected characteristics of current infusion pumping operation, wherein said characteristics of current infusion pumping operation are selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, maximum dose limit, minimum dose limit, minimum volume to be infused, maximum volume to be infused, patient weight, and patient height;
   (b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;
   (c) a wireless signal pump transmitter connected to said pump operation circuitry in said IV medication infusion pump for transmitting at least one wireless signal representing said pre-selected monitored current pumping operation characteristics;
   (d) an HIMS receiver capable of receiving said at least one wireless signal representing said pumping operation characteristics said receiver connected to said hospital management system (HIMS) for receiving said current pumping operation characteristics represented by said at least one wireless signal from said IV pump, said HIMS receiver further capable of receiving said signal representing said doctor's order;
   (e) a pharmacy receiver for receiving said doctor's order signal representing said doctor's order, said pharmacy receiver operatively connected to a program and a display to provide human readable information sufficient for a pharmacist to prepare the ordered medication;
   (f) a pharmacy transmitter for sending a delivery signal indicating that an IV medication has been delivered to a nurses station and representing that the IV medication is to be administered to a patient according to said doctor's order;
   (g) wherein said HIMS further comprises programming for receiving, storing and comparing said pump signal with said signal representing said doctor's order to determine whether said medication is delivered to said patient by operation of said pump according to said doctor's order;
   (h) wherein said HIMS further comprises programming for storing said delivery signal and for comparing said delivery signal to said order signal and/or to said pump operation characteristics signal to facilitate monitoring of the timely delivery of the IV medication to the patient according to the doctor's order and to provide a wireless signal received and displayed at the pump representing the order signal;
   (i) wherein said operation circuitry comprises user authorization code input circuitry at the IV pump wherein a user authorization code is required to be input at said IV pump prior to uploading said doctor's order provided by said signal representing said doctor's order received from said HIMS; and
   (j) said operation circuitry comprises validation circuitry requiring manual validation of said doctor's order and said pump operation characteristics, by manual activation of said pump operation at the IV pump following said display of said wirelessly transmitted doctor's order signal from said HIMS.

2. A wireless communication system from an IV medication infusion pump to a hospital information management system (HIMS) comprising:
   (a) pump operation circuitry in said IV medication infusion pump for operating said IV medication infusion pump and for continuously monitoring pre-selected characteristics of current infusion pumping operation, wherein said characteristics of current infusion pumping operation are selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, maximum dose limit, minimum dose limit, minimum volume to be infused, maximum volume to be infused, patient weight, and patient height;
   (b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;
   (c) a wireless signal pump transmitter connected to said pump operation circuitry in said IV medication infusion pump for transmitting at least one wireless signal representing said pre-selected monitored current pumping operation characteristics;
(d) an HIMS receiver capable of receiving said at least one wireless signal representing said pumping operation characteristics, said receiver connected to said hospital management system (HIMS) for receiving said current pumping operation characteristics represented by said at least one wireless signal from said IV pump, said HIMS receiver further capable of receiving said signal representing said doctor's order;
(e) a laboratory or blood bank receiver for receiving said order signal when a blood product IV is ordered for the patient;
(f) a laboratory or blood bank signal transmitter for signaling to said HIMS the delivery of a blood product for IV administration to a patient and including information related to the time sensitivity of the blood product;
(g) wherein said HIMS further comprises programming for receiving, storing and comparing said pump signal with said signal representing said doctor's order to determine whether said medication is delivered to said patient by operation of said pump according to said doctor's order;
(h) wherein said HIMS further comprises programming for comparing said laboratory signal to said pump operation characteristics signal so that actual timely delivery of said blood product represented by said laboratory signal can be monitored and the results of the comparison can be displayed, and to provide a wireless signal received and displayed at the IV pump representing the laboratory signal;
(i) wherein said operation circuitry comprises user authorization code input circuitry at the IV pump wherein a user authorization code is required to be input at said IV pump prior to uploading said laboratory signal provided by said at least one wireless signal from said HIMS representing the comparison of the laboratory signal; and
(j) said operation circuitry comprises validation circuitry requiring manual validation of said laboratory signal and said pump operation characteristics signal, and activation circuitry requiring manual activation of said pump operation at the IV pump following said display of said wirelessly transmitted laboratory signal from said HIMS.

3. A wireless communication system from an IV medication infusion pump to a hospital information management system (HIMS) comprising:
(a) pump operation circuitry in said IV medication infusion pump for operating said IV medication infusion pump and for continuously monitoring pre-selected characteristics of current infusion pumping operation, wherein said characteristics of current infusion pumping operation are selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, maximum dose limit, minimum dose limit, minimum volume to be infused, maximum volume to be infused, patient weight, and patient height;
(b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;
(c) a wireless signal pump transmitter connected to said pump operation circuitry in said IV medication infusion pump for transmitting at least one wireless signal representing said pre-selected monitored current pumping operation characteristics;
(d) an HIMS receiver capable of receiving said at least one wireless signal representing said pumping operation characteristics, said receiver connected to said hospital management system (HIMS) for receiving said current pumping operation characteristics represented by said at least one wireless signal from said IV pump, said HIMS receiver further capable of receiving said signal representing said doctor's order;
(e) wherein said HIMS further comprises programming for receiving, storing and comparing said pump signal with said signal representing said doctor's order to determine whether said medication is delivered to said patient by operation of said pump according to said doctor's order;
(f) wherein said transmitter connected to said pump comprises a transceiver for receiving signals corresponding to pumping operation characteristics according to said doctor's order for medication to a patient;
(g) wherein said HIMS receiver comprises a transceiver for receiving said doctor's order and for transmitting another signal representing pumping operation characteristics corresponding to said doctor's ordered medication for a patient, and to provide a wireless signal received and displayed at the IV pump representing the pumping operation characteristics according to said doctor's order signal;
(h) wherein the authorization code is required prior to downloading said pumping operation characteristics according to said doctor's order signal and the pump operation characteristics signal provided by said at least one wireless signal from said HIMS and further comprising a display of said doctor's order; and
(i) wherein said operation circuitry comprises validation circuitry requiring manual validation of said pumping operation characteristics according to said doctor's order, and activation circuitry requiring manual activation of said pump operation at the IV pump following said display of said wirelessly transmitted pumping operation characteristics according to said doctor's order signal.

4. A wireless communication system from an IV medication infusion pump to a hospital information management system (HIMS) comprising:
(a) pump operation circuitry in said IV medication infusion pump for operating said IV medication infusion pump and for continuously monitoring pre-selected characteristics of current infusion pumping operation, wherein said characteristics of current infusion pumping operation are selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, maximum dose limit, minimum dose limit, minimum volume to be infused, maximum volume to be infused, patient weight, and patient height;

(b) a medication order transmitter capable of receiving input of a doctor's order for patient medication to be administered with an IV pump and capable of wireless transmission of an order signal representing said doctor's order for said patient medication for IV administration comprising at least one pumping operation parameter corresponding to said doctor's input order;

(c) a wireless signal pump transmitter connected to said pump operation circuitry in said IV medication infusion pump for transmitting at least one wireless signal representing said pre-selected monitored current pumping operation characteristics;

(d) an HIMS receiver capable of receiving said at least one wireless signal representing said pumping operation characteristics, said receiver connected to said hospital management system (HIMS) for receiving said current pumping operation characteristics represented by said at least one wireless signal from said IV pump, said HIMS receiver further capable of receiving said signal representing said doctor's order;

(e) a nurses station transmitter having an input for entry of information on IV medication received at a nurses station and for transmitting a medicine received signal representing the IV medications received for a patient upon receiving any ordered medication;

(f) wherein said HIMS further comprises programming for receiving, storing and comparing said pump signal with said signal representing said doctor's order to determine whether said medication is delivered to said patient by operation of said pump according to said doctor's order;

(g) wherein said HIMS further comprises programming for receiving and storing said IV medication received signal and for comparing said medication received signal with at least one of said order signal and said pumping characteristics signal to facilitate monitoring of preparation, delivery and administration of said IV medication and for providing the results and to provide a wireless signal received and displayed at the IV pump representing the IV medication received signal;

(h) wherein said operation circuitry comprises user authorization code input circuitry at the IV pump and wherein the authorization code is required prior to downloading said IV medication received signal provided by said at least one wireless signal from said HIMS and further comprising a display of said IV medication received signal; and (i) said operation circuitry comprises validation circuitry requiring manual validation of said IV medication received signal, and activation circuitry requiring manual activation of said pump operation at the IV pump following said display of said wirelessly transmitted IV medication received signal.

5. A wireless communication system from an IV medication infusion pump to a hospital information management system (HIMS) comprising:

(a) a medication order transmitter capable of receiving input of a doctor's order for patient medication to be administered with an IV pump and capable of wireless transmission of a first signal representing the input order for said patient medication for IV administration;

(b) an IV pump having pump operation circuitry for monitoring pre-selected characteristics of pump operation and a transmitter connected to said pump operation circuitry for transmitting a second wireless signal representing said pre-selected pump operation characteristics indicative of IV administration of medication to a patient, wherein said characteristics of current infusion pumping operation are selected from among rate of pumping, pumping pressure, start time, time of pumping, volume of pumping, dosage, size of tubing, speed of pumping motor, door open, manual programming mode, automatic programming mode, start-up testing, dosage of infusion and bolus of infusion, nurse identification, unique patient identification, a drug name, total volume of infusion, current date, current time, maximum dose limit, minimum dose limit, minimum volume to be infused, maximum volume to be infused, patient weight, and patient height;

(c) a receiver for receiving said first signal and for providing said order for patient medication in human readable form for the preparation of said ordered patient medication for IV pump administration;

(d) a hospital information system including a receiver capable of receiving said first and said second signals and a computer processor capable of storing said information represented by said signals, capable of comparing said doctor's order for patient medication to said IV pump delivery of medication to a patient and for comparing said order to said current administration characteristics to determine whether medication delivery was as ordered by the doctor and for displaying said order and said pump operation characteristics and the results of the comparison thereof and to provide a third wireless signal received and displayed at the IV pump representing a confirmed doctor's order for medication to be delivered;

(e) wherein said operation circuitry comprises user authorization code input circuitry at the IV pump, wherein an authorization code is required prior to downloading said confirmed doctor's order for delivery provided by said third wireless signal from said HIMS representing the confirmed doctor's order signal and further comprising a display of said confirmed doctor's order for medication to be delivered; and (f) said operation circuitry comprises validation circuitry requiring manual validation of said confirmed doctor's order for patient medication for IV administration, and activation circuitry requiring manual activation of said pump operation at the IV pump following said display of said wirelessly transmitted confirmed doctor's order for patient medication for IV administration.

* * * * *